(12) United States Patent
Fernald et al.

(10) Patent No.: US 7,624,651 B2
(45) Date of Patent: Dec. 1, 2009

(54) APPARATUS AND METHOD FOR ATTENUATING ACOUSTIC WAVES IN PIPE WALLS FOR CLAMP-ON ULTRASONIC FLOW METER

(75) Inventors: Mark Fernald, Enfield, CT (US); Daniel L. Gysling, Glastonbury, CT (US); Timothy J. Bailey, Longmeadow, MA (US); Changjiu Dang, Wallingford, CT (US)

(73) Assignee: Expro Meters, Inc., Wallingford, CT (US)

( * ) Notice: Subject to any disclaimer, the term of this patent is extended or adjusted under 35 U.S.C. 154(b) by 0 days.

(21) Appl. No.: 11/926,757

(22) Filed: Oct. 29, 2007

(65) Prior Publication Data

US 2008/0098818 A1 May 1, 2008

Related U.S. Application Data

(60) Provisional application No. 60/855,585, filed on Oct. 30, 2006.

(51) Int. Cl.
G01F 1/66 (2006.01)
(52) U.S. Cl. .................................................. 73/861.27
(58) Field of Classification Search .............. 73/861.29, 73/861.27, 861.28, 861.25, 861.26
See application file for complete search history.

(56) References Cited

U.S. PATENT DOCUMENTS

| | | | |
|---|---|---|---|
| 2,874,568 | A | 2/1959 | Petermann |
| 3,715,709 | A | 2/1973 | Zacharias et al. |
| 3,751,979 | A | 8/1973 | Ims |
| 3,781,895 | A | 12/1973 | Monser |
| 3,851,521 | A | 12/1974 | Ottenstein |
| 3,885,432 | A | 5/1975 | Herzl |
| 3,952,578 | A | 4/1976 | Jacobs |
| 4,004,461 | A | 1/1977 | Lynworth |
| 4,004,465 | A | 1/1977 | Lynworth |

(Continued)

FOREIGN PATENT DOCUMENTS

DE  4306119  9/1994

(Continued)

OTHER PUBLICATIONS

Sonar-Based Volumetric Flow Meter For Pulp and Paper Applications—Daniel L. Gysling & Douglas H. Loose—Dec. 13, 2003.

(Continued)

*Primary Examiner*—Jewel Thompson

(57) ABSTRACT

An apparatus is presented for damping an undesired component of an ultrasonic signal. The apparatus includes a sensor affixed to a pipe. The sensor includes a transmitter and a receiver. The transmitted ultrasonic signal includes a structural component propagating through the pipe and a fluid component propagating through a flow in the pipe. The receiver receives one of the transmitted components. The apparatus includes a damping structure. The damping structure dampens the structural component of the ultrasonic signal to impede propagation of the structural component to the receiver. The damping structure includes one of a housing secured to the pipe to modify ultrasonic vibrational characteristics thereof, a plurality of film assemblies including a tunable circuit to attenuate structural vibration of the pipe, and a plurality of blocks affixed to the pipe to either reflect or propagates through the blocks, the undesired structural component of the ultrasonic signal.

17 Claims, 23 Drawing Sheets

U.S. PATENT DOCUMENTS

| | | | |
|---|---|---|---|
| 4,032,259 A | 6/1977 | Brown | |
| 4,080,837 A | 3/1978 | Alexander et al. | |
| 4,195,517 A | 4/1980 | Kalinoski et al. | |
| 4,248,085 A | 2/1981 | Coulthard | |
| 4,320,659 A | 3/1982 | Lynnworth et al. | |
| 4,445,389 A | 5/1984 | Potzick et al. | |
| 4,520,320 A | 5/1985 | Potzick et al. | |
| 4,561,310 A | 12/1985 | Barnard et al. | |
| 4,677,305 A | 6/1987 | Ellinger | |
| 4,717,159 A | 1/1988 | Alston et al. | |
| 4,896,540 A | 1/1990 | Shakkottai et al. | |
| 4,932,262 A | 6/1990 | Wlodarczyk | |
| 5,040,415 A | 8/1991 | Barkhoudarian | |
| 5,060,506 A | 10/1991 | Douglas | |
| 5,083,452 A | 1/1992 | Hope | |
| 5,218,197 A | 6/1993 | Carroll | |
| 5,285,675 A | 2/1994 | Colgate et al. | |
| 5,289,726 A | 3/1994 | Miau et al. | |
| 5,359,897 A | 11/1994 | Hamstead et al. | |
| 5,363,342 A | 11/1994 | Layton et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,591,922 A | 1/1997 | Segeral et al. | |
| 5,625,140 A | 4/1997 | Cadet et al. | |
| 5,708,211 A | 1/1998 | Jepson et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,856,622 A | 1/1999 | Yamamoto et al. | |
| 5,948,959 A | 9/1999 | Peloquin | |
| 6,016,702 A | 1/2000 | Maron | |
| 6,062,091 A * | 5/2000 | Baumoel | 73/861.27 |
| 6,069,069 A | 5/2000 | Gysling | |
| 6,151,958 A | 11/2000 | Letton et al. | |
| 6,202,494 B1 | 3/2001 | Riebel et al. | |
| 6,233,374 B1 | 5/2001 | Ogle et al. | |
| 6,261,232 B1 | 7/2001 | Yokosawa et al. | |
| 6,345,539 B1 | 2/2002 | Rawes et al. | |
| 6,349,599 B1 | 2/2002 | Lynnworth et al. | |
| 6,354,147 B1 | 3/2002 | Gysling et al. | |
| 6,378,357 B1 | 4/2002 | Han et al. | |
| 6,397,683 B1 | 6/2002 | Hagenmeyer | |
| 6,412,353 B1 | 7/2002 | Kleven et al. | |
| 6,435,030 B1 | 8/2002 | Gysling et al. | |
| 6,442,996 B1 | 9/2002 | Thurston et al. | |
| 6,443,226 B1 | 9/2002 | Diener et al. | |
| 6,450,037 B1 | 9/2002 | McGuinn et al. | |
| 6,463,813 B1 | 10/2002 | Gysling | |
| 6,532,827 B1 | 3/2003 | Ohnishi | |
| 6,536,291 B1 | 3/2003 | Gysling | |
| 6,550,342 B2 | 4/2003 | Croteau et al. | |
| 6,558,036 B2 | 5/2003 | Gysling et al. | |
| 6,584,862 B1 * | 7/2003 | Molenaar | 73/861.27 |
| 6,587,798 B2 | 7/2003 | Kersey et al. | |
| 6,601,005 B1 | 7/2003 | Eryurek et al. | |
| 6,601,458 B1 | 8/2003 | Gysling et al. | |
| 6,609,069 B2 | 8/2003 | Gysling | |
| 6,626,049 B1 * | 9/2003 | Ao | 73/861.29 |
| 6,672,163 B2 | 1/2004 | Han et al. | |
| 6,691,584 B2 | 2/2004 | Gysling et al. | |
| 6,698,297 B2 | 3/2004 | Gysling | |
| 6,715,366 B2 * | 4/2004 | Ohnishi | 73/861.27 |
| 6,723,575 B2 | 4/2004 | Gysling et al. | |
| 6,732,575 B2 | 5/2004 | Gysling et al. | |
| 6,773,603 B2 | 8/2004 | Moorehead et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,837,332 B1 | 1/2005 | Rodney | |
| 6,862,920 B2 | 3/2005 | Gysling et al. | |
| 6,889,562 B2 | 5/2005 | Gysling et al. | |
| 6,898,541 B2 | 5/2005 | Gysling et al. | |
| 6,971,259 B2 | 12/2005 | Gysling | |
| 6,988,411 B2 | 1/2006 | Gysling et al. | |
| 7,000,485 B2 * | 2/2006 | Ao et al. | 73/861.29 |
| 7,032,432 B2 | 4/2006 | Gysling et al. | |
| 2002/0123852 A1 | 9/2002 | Gysling et al. | |
| 2002/0129662 A1 | 9/2002 | Gysling et al. | |
| 2003/0038231 A1 | 2/2003 | Davis et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0006509 A1 | 1/2004 | Liljenberg et al. | |
| 2004/0011141 A1 | 1/2004 | Lynnworth | |
| 2004/0016284 A1 | 1/2004 | Gysling et al. | |
| 2004/0069069 A1 | 4/2004 | Croteau et al. | |
| 2004/0074312 A1 | 4/2004 | Gysling et al. | |
| 2004/0144182 A1 | 7/2004 | Gysling et al. | |
| 2004/0167735 A1 | 8/2004 | Rothman et al. | |
| 2004/0168522 A1 | 9/2004 | Bailey et al. | |
| 2004/0168523 A1 | 9/2004 | Bailey et al. | |
| 2004/0194539 A1 | 10/2004 | Gysling | |
| 2004/0199340 A1 | 10/2004 | Kersey et al. | |
| 2004/0199341 A1 | 10/2004 | Gysling et al. | |
| 2004/0210404 A1 | 10/2004 | Gysling et al. | |
| 2004/0226386 A1 | 11/2004 | Croteau et al. | |
| 2004/0231431 A1 | 11/2004 | Bailey et al. | |
| 2004/0255695 A1 | 12/2004 | Gysling | |
| 2005/0000289 A1 | 1/2005 | Gysling et al. | |
| 2005/0005711 A1 | 1/2005 | Gysling et al. | |
| 2005/0005712 A1 | 1/2005 | Gysling et al. | |
| 2005/0005713 A1 | 1/2005 | Winston et al. | |
| 2005/0005912 A1 | 1/2005 | Gysling et al. | |
| 2005/0011258 A1 | 1/2005 | Gysling et al. | |
| 2005/0011283 A1 | 1/2005 | Gysling et al. | |
| 2005/0011284 A1 | 1/2005 | Davis et al. | |
| 2005/0012935 A1 | 1/2005 | Kersey | |
| 2005/0016284 A1 | 1/2005 | Gysling et al. | |
| 2005/0033545 A1 | 2/2005 | Gysling | |
| 2005/0039520 A1 | 2/2005 | Davis et al. | |
| 2005/0044929 A1 | 3/2005 | Gysling et al. | |
| 2005/0044966 A1 | 3/2005 | Gysling et al. | |
| 2005/0050956 A1 | 3/2005 | Gysling et al. | |
| 2005/0061060 A1 | 3/2005 | Banach et al. | |
| 2005/0072216 A1 | 4/2005 | Engel | |
| 2005/0125166 A1 | 6/2005 | Loose et al. | |
| 2005/0125170 A1 | 6/2005 | Gysling | |
| 2005/0171710 A1 | 8/2005 | Gysling et al. | |

FOREIGN PATENT DOCUMENTS

| | | |
|---|---|---|
| EP | 0290336 | 11/1998 |
| EP | 1186868 | 3/2002 |
| GB | 2210169 | 6/1989 |
| WO | WO 9314382 | 7/1993 |
| WO | WO 9967629 | 12/1999 |
| WO | WO 0000793 | 1/2000 |
| WO | WO 00/46583 | 8/2000 |
| WO | WO 0102810 | 1/2001 |
| WO | WO 02/50511 | 6/2002 |
| WO | WO 2004/063741 | 7/2004 |

OTHER PUBLICATIONS

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

Piezo Film Sensors Technical Manual—Measurement Specialties Inc.—Sensor Products Division Apr. 2, 1999.
http://en.wikipedia.org/wiki//Convection, p. 1-5.
www.m-w.com/dictionary/acoustic.
Harshal B. Nemade, IEEE Transactions on Instrumentation and Measurement, vol. 47, No. 1, Feb. 1998, p. 265-269.
"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.
"Development of an array of pressure sensors with PVDF film, Experiments in Fluids 26", Jan. 8, 1999, Springer-Verlag.
"Viscous Attentuation of Acoustic Waves in Suspensions" by R.L. Gibson, Jr. and M.N. Toksoz.

* cited by examiner

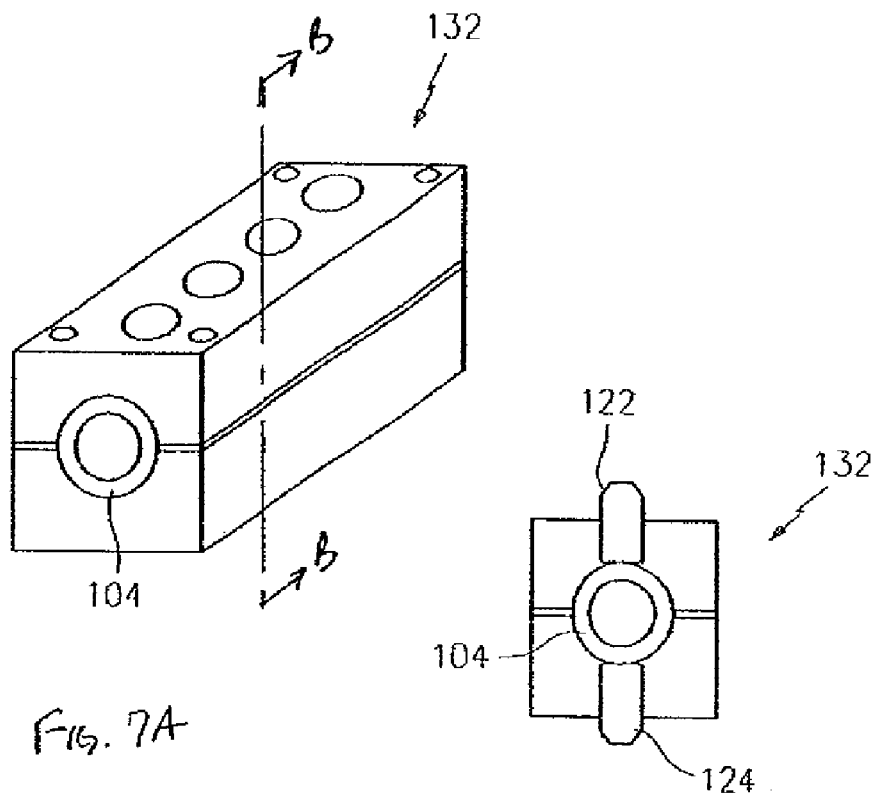
FIG. 7A
FIG. 7B
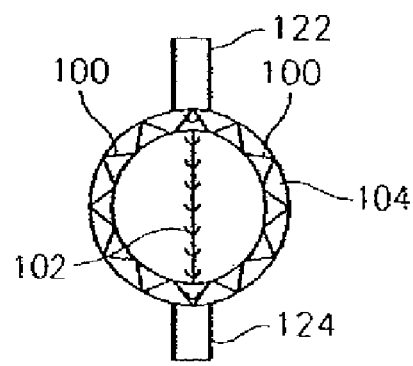
FIG. 8

| Wall thickness (in) | a Diaphragm Dia (in) | Transmission and Diaphragm Freq (KHz) |
|---|---|---|
| 0.25 | 0.5 | 401 |
| 0.3 | 0.6 | 334 |
| 0.4 | 0.8 | 251 |
| 0.5 | 1 | 200 |
| 1 | 2 | 100 |

*FIG. 9B*

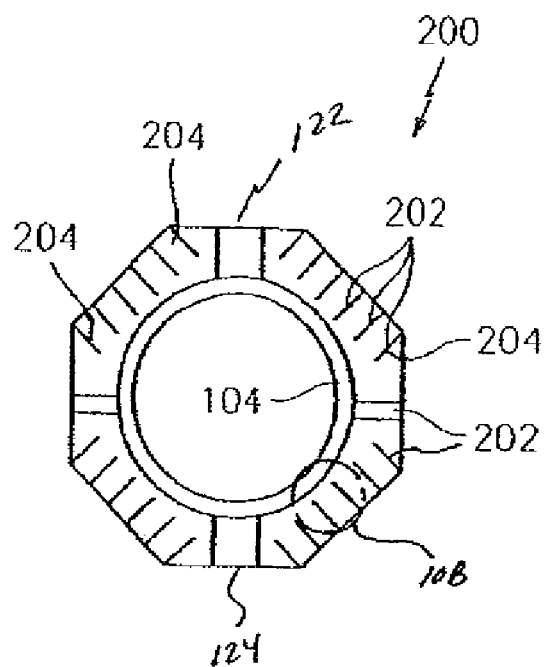
FIG. 10A
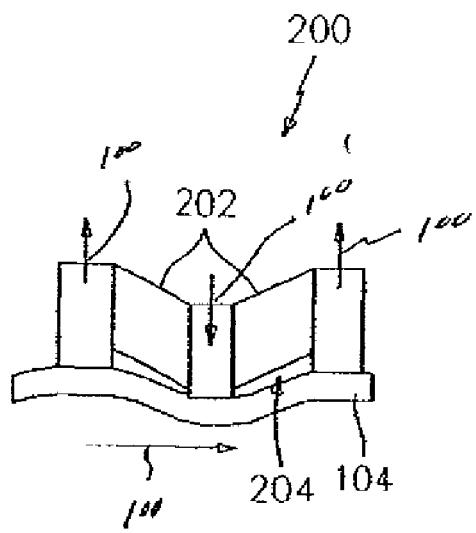
FIG. 10B
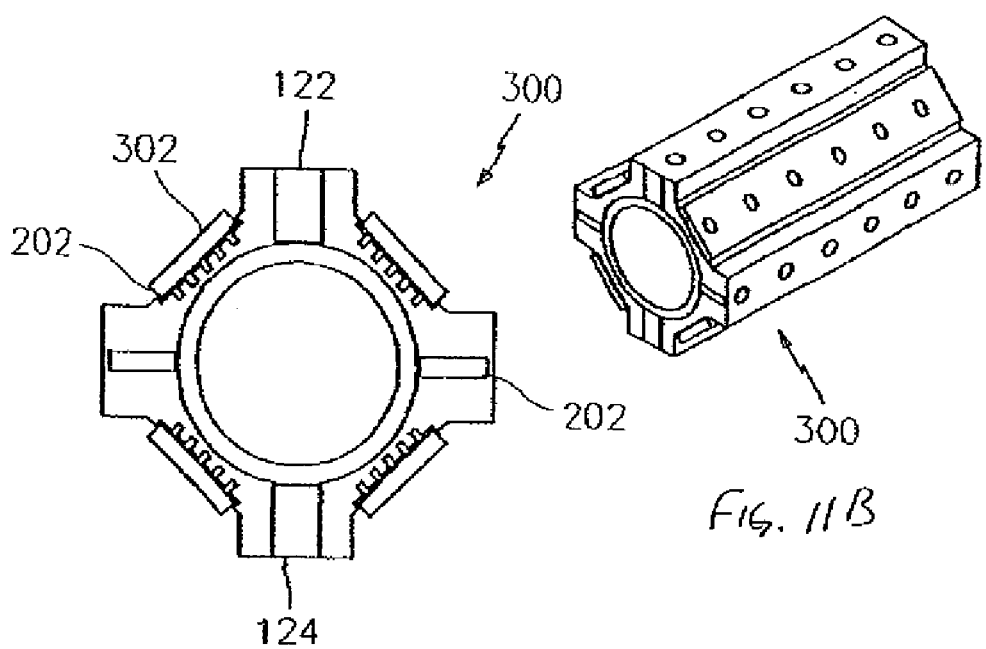
FIG. 11A
FIG. 11B

APPARATUS AND METHOD FOR ATTENUATING ACOUSTIC WAVES IN PIPE WALLS FOR CLAMP-ON ULTRASONIC FLOW METER

This application claims the benefit of U.S. Provisional Patent Application Ser. No. 60/855,585, filed Oct. 30, 2006.

CROSS-REFERENCE TO RELATED PATENT APPLICATIONS

This application is also related to U.S. patent application Ser. No. 11/881,477, filed Jul. 27, 2007. The disclosures of these U.S. patent documents are incorporated by reference herein in their entireties.

TECHNICAL FIELD

This invention relates to a method and apparatus for attenuating acoustic waves (or ring around acoustics) propagating through the walls of a pipe for a clamp-on ultrasonic flow meter.

BACKGROUND

Most ultrasonic flow measurements seek to leverage information contained in fluid borne disturbances of a specific temporal frequency. The specific frequency often results from natural frequencies of the drive electronics, the transducer, or the resonant transmission characteristic of the pipe wall.

Referring to FIG. 8, one of the primary challenges associated with clamp-on ultrasonic flow metering is the interference between the structural borne ultrasonic signal component 100 and the desired fluid borne ultrasonic signal component 102. The structural borne component 100 of the ultrasonic signal is often of the same or similar frequency and essentially masks the fluid borne component 102 of the ultrasonic signal.

Standard pipes are fairly effective waveguides for structural borne acoustics components 100. The ultrasonic pulse propagates along the wall of a pipe 104 with very little damping and rings around the circumference numerous times until the inherent damping in the pipe and the propagation of energy axially away from the initial excitation eventually dissipates the structural borne ultrasonic waves.

SUMMARY OF THE INVENTION

In one aspect of the present invention, an apparatus is presented for damping at least one component of an ultrasonic signal. The apparatus includes at least one sensor affixed to an outer surface of a pipe. The sensor includes a transmitter and a receiver. The transmitter transmits the ultrasonic signal. The transmitted ultrasonic signal includes a structural component that propagates through a wall of the pipe, and a fluid component that propagates through a process flow in the pipe. The receiver receives at least one of the transmitted components of the ultrasonic signal. The apparatus also includes a damping structure affixed to the pipe. The damping structure dampens the structural component of the ultrasonic signal to impede propagation of the structural component to the receiver.

In one embodiment, the damping structure includes a housing secured to the pipe to modify ultrasonic vibrational characteristics of the pipe by increasing a flexural stiffness of the pipe. In this regard, the housing contacts and reinforces selective areas of the pipe to provide a diaphragm including reinforced areas and unreinforced areas. The unreinforced areas are disposed about and in proximity to the transmitter and the receiver. In one embodiment, a resonant frequency of the diaphragm coincides with a resonant frequency of a maximum transmission of the ultrasonic signal.

In another embodiment, the damping structure includes a plurality of film assemblies applied to an outer surface of the pipe. Each of the film assemblies includes a substrate and a selectively tunable circuit. The circuit is tuned to attenuate structural vibration of the pipe and the structural component propagating in the wall of the pipe. In one embodiment, the substrate is comprised of a piezoelectric film and the tunable circuit is comprised of a RLC circuit.

In yet another embodiment, the damping structure includes a plurality of blocks affixed to the pipe. The blocks and the pipe wall are at different impedances such that the structural component of the ultrasonic signal is either reflected back toward the transmitter, or propagates through a dissipation path in the blocks and away from the receiver. In one embodiment, the blocks are disposed axially along the pipe between the transmitter and the receiver. In another embodiment, one of the blocks is disposed between the pipe wall and the transmitter and another of the blocks is disposed between the pipe wall and the receiver.

In still another embodiment, the damping apparatus of the present invention includes a processor coupled to the receiver. The processor samples the received components of the ultrasonic signal and processes the sampled signal to determine a parameter of the process flow in the pipe.

BRIEF DESCRIPTION OF THE DRAWINGS

Referring now to the drawing wherein like items are numbered alike in the various Figures.

FIGS. 7A and 7B are a perspective view and a cross-sectional view along line B-B of FIG. 7A, respectively, illustrating an embodiment of a structurally significant housing clamped on to a pipe, in accordance with the present invention.

FIG. 8 is a cross-sectional view of structurally borne and fluid borne components propagating through a pipe wall having an ultrasonic sensor attached thereto.

FIG. 9B is a table illustrating diaphragm diameter and ultrasonic frequency as a function of wall thickness.

FIGS. 10A and 10B are a cross-sectional view and an expanded view about circle 10B of a structurally significant housing in accordance with another embodiment of the present invention.

FIGS. 11A and 11B are a cross-sectional view and a perspective view of a structurally significant housing in accordance with another embodiment of the present invention.

DETAILED DESCRIPTION OF PREFERRED EMBODIMENTS OF THE INVENTION

The present invention discloses apparatus' and methods for reducing the impact of structural borne noise, an unintended by-product of launching a fluid borne ultrasonic interrogation signal, during the operation of clamp-on flow ultrasonic flow meters, as described in commonly owned, U.S. patent application Ser. No. 10/756,977, filed Jan. 13, 2004, which is incorporated herein by reference.

Figure 1:
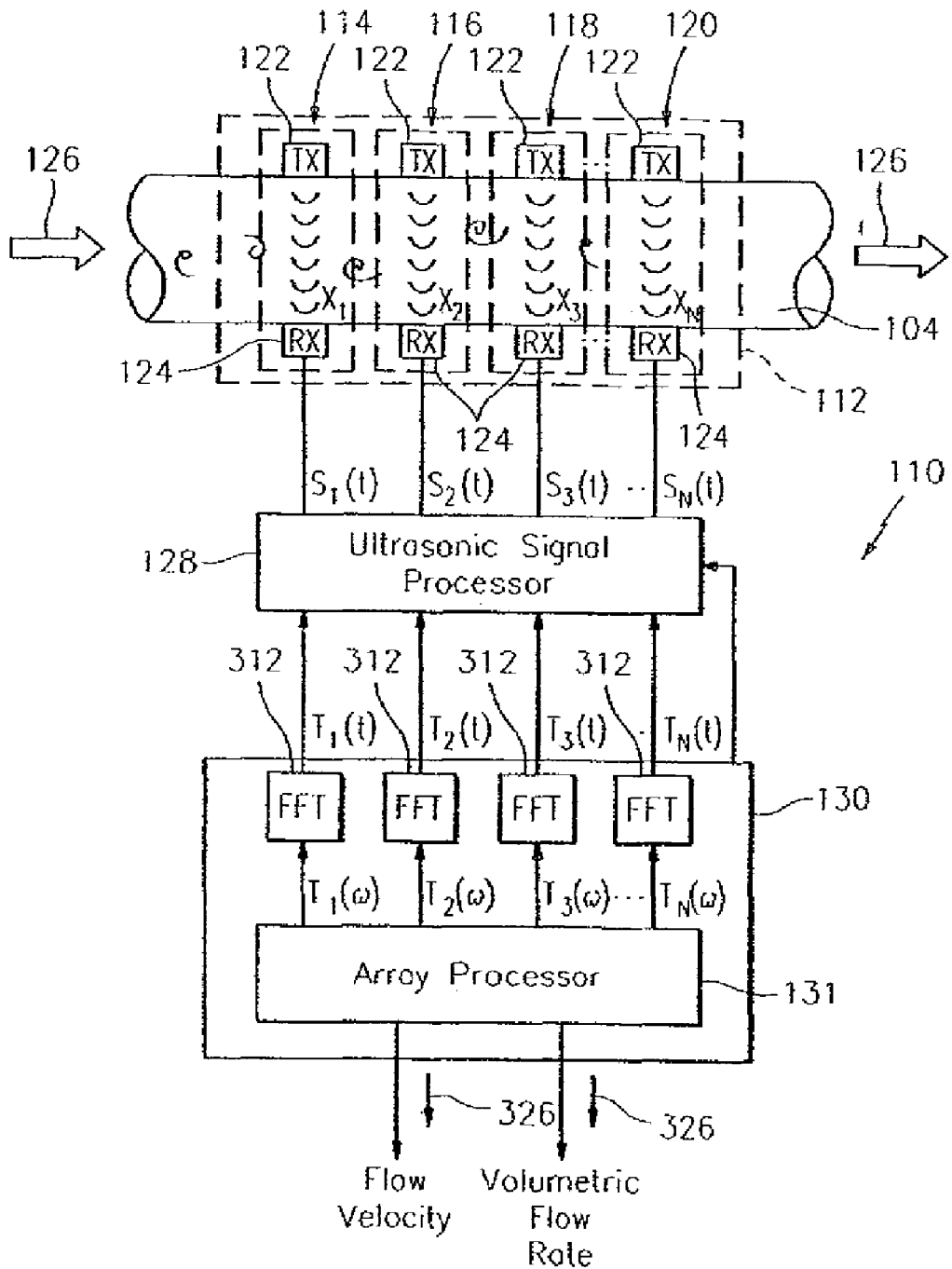
FIG. 1 is a block diagram of a flow meter having an array of ultrasonic sensor units disposed axially along a pipe for measuring the volumetric flow of the fluid flowing in the pipe, in accordance with the present invention.
Figure 2:
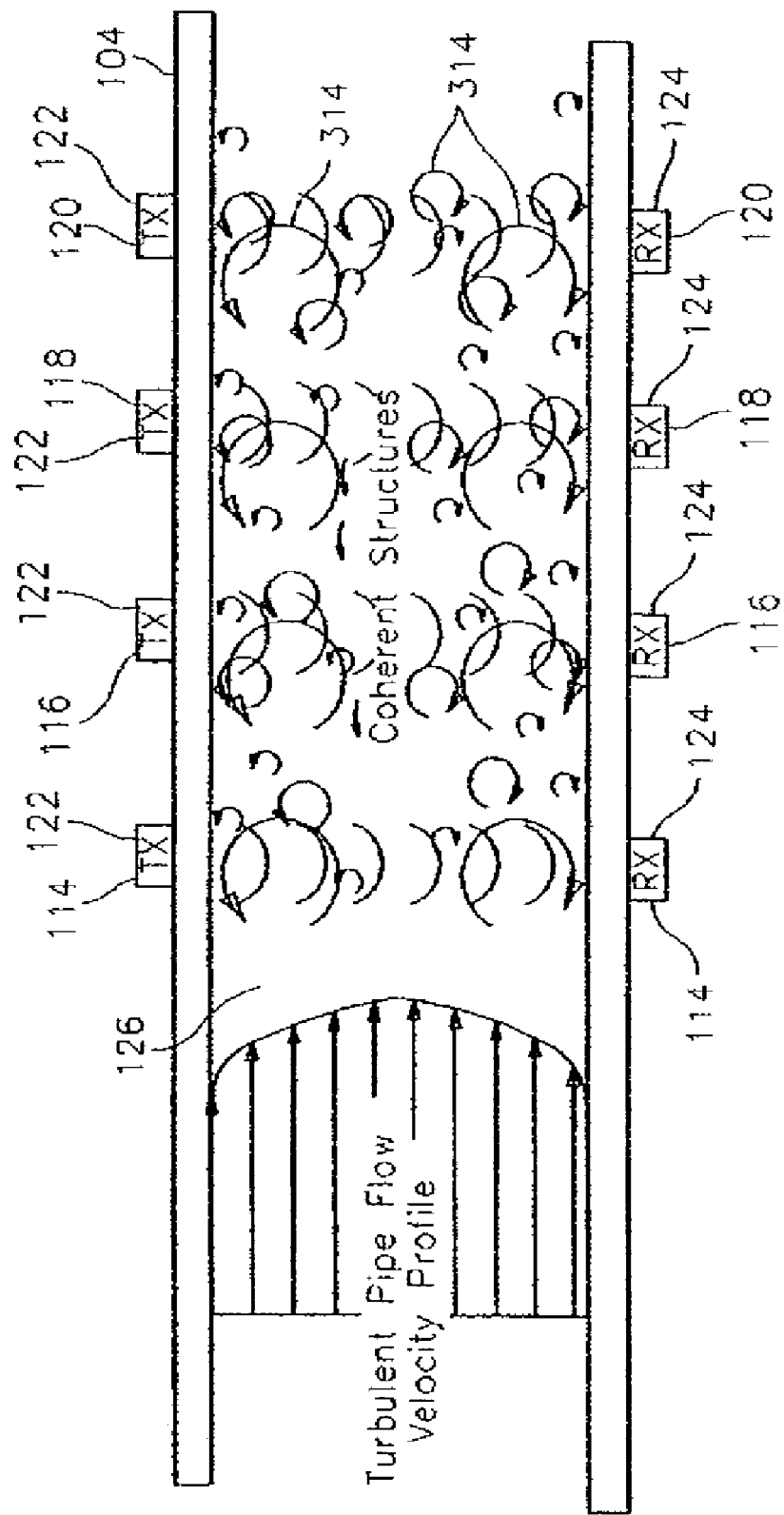
FIG. 2 is a cross-sectional view of a pipe having a turbulent flow including coherent structures therein, in accordance with the present invention.

FIGS. 1 and 2 illustrate an ultrasonic clamp-on flow meter 110, as described in U.S. patent application Ser. No. 10/756,977, wherein the ultrasonic flow meter 110 includes an array of ultrasonic sensors 112 (e.g., a sensing device 112) having a plurality of ultrasonic sensors 114, 116, 118 and 120 disposed axially along the length of a pipe 104. Each ultrasonic sensor 114, 116, 118 and 120 comprises a transmitter (TX) 122 and a receiver (RX) 124 pair. The transmitter 122 provides an ultrasonic signal to the corresponding receiver 124, wherein the ultrasonic signal is orthogonal to a direction of the flow of a fluid 126. While this embodiment of the present clamp-on ultrasonic meter 110 is described, one will appreciate that the present invention is applicable to the other embodiments, such as that described and taught in U.S. patent application Ser. No. 10/756,977, including embodiments in non-orthogonal ultrasonic signals, pitch and catch configurations, pulse echo configurations, and combined transmitter/receiver ultrasonic sensors, as shown in FIGS. 3-6.

Figure 3:
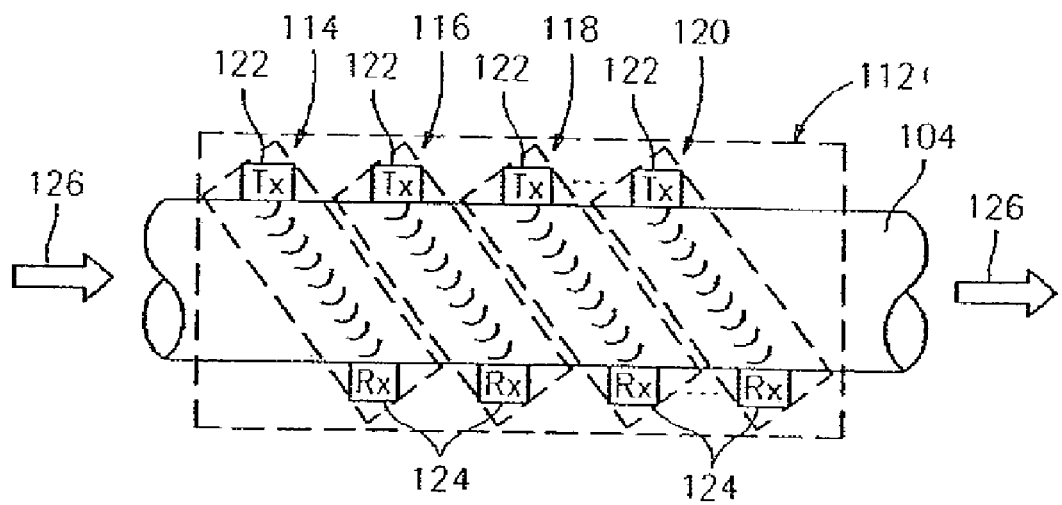
FIG. 3 is a block diagram of an alternative embodiment of a sensing device of a flow meter embodying the present invention similar to that shown in FIG. 1.

For example, while each of the ultrasonic sensor units 114, 116, 118 and 120 comprises a pair of ultrasonic sensors (transmitter and receiver) 122, 124 that are diametrically-opposed to provide through transmission, the present invention contemplates that one of the ultrasonic sensors 122, 124 of each sensor unit 114, 116, 118 and 120 may be offset axially along the pipe 104 such that the ultrasonic signal from the transmitter sensor 122 has an axial component in its propagation direction, as shown in FIG. 3.

Figure 4:
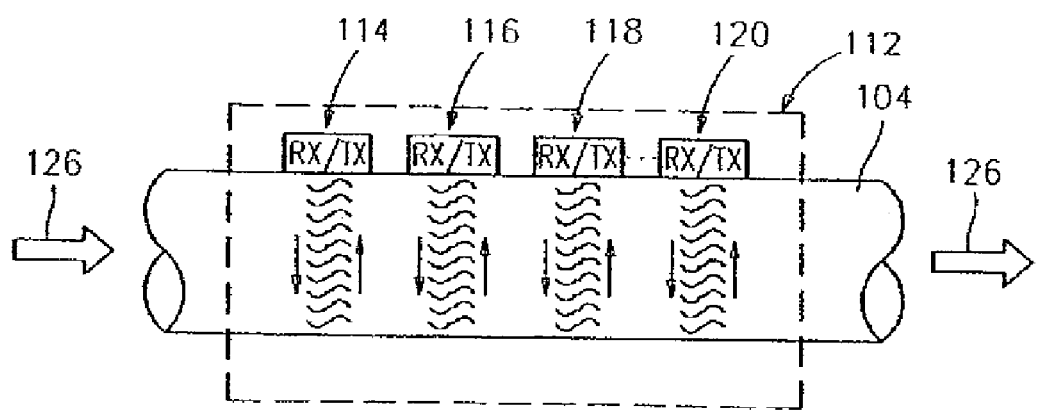
FIG. 4 is a block diagram of an alternative embodiment of a sensing device of a flow meter embodying the present invention similar to that shown in FIG. 1.

As shown in FIG. 4, the present invention also contemplates that the sensor units 114, 116, 118 and 120 of the sensing device 112 may be configured in a pulse/echo configuration. In this embodiment, each sensing unit 114, 116, 118 and 120 comprises one ultrasonic sensor that transmits an ultrasonic signal through the pipe wall and fluid 126 substantially orthogonal to the direction of the fluid flow and receives a reflection of the ultrasonic signal reflected back from the wall of the pipe to the ultrasonic sensor.

Figure 5:
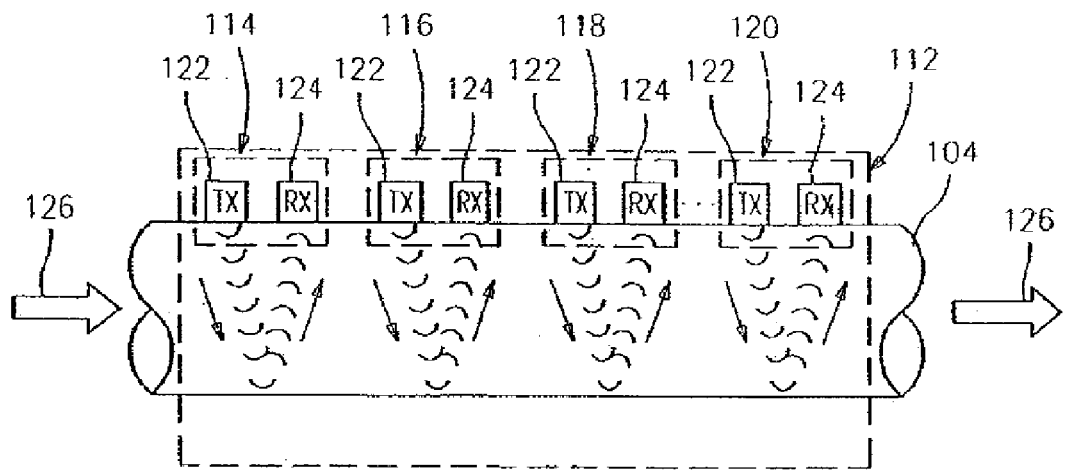
FIG. 5 is a block diagram of an alternative embodiment of a sensing device of a flow meter embodying the present invention similar to that shown in FIG. 1.

Referring to FIG. 5, the sensing device 112 may be configured to function in a pitch and catch configuration. In this embodiment, each sensor unit 114, 116, 118 and 120 comprises a pair of ultrasonic sensors (transmitter, receiver) 122, 124 disposed axially along the pipe 104 disposed on a same side of the pipe 104 at a predetermined distance apart. Each transmitter sensor 122 provides an ultrasonic signal at a predetermined angle into the flow 126. The ultrasonic signal propagates through the fluid 126 and reflects off of an inner surface of the pipe 104 which reflects the ultrasonic signal back through the fluid 126 to a receiver sensor 124 in the respective pair of sensors 122, 124.

Figure 6:
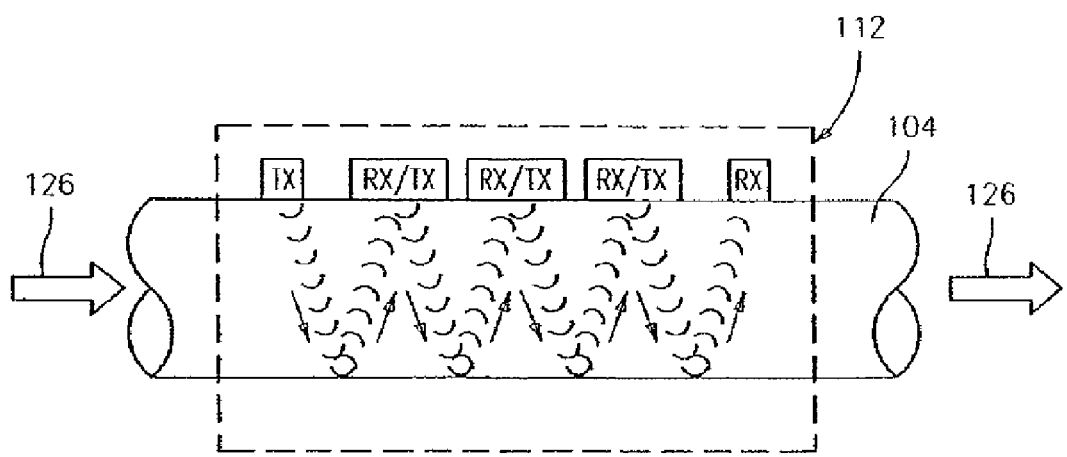
FIG. 6 is a block diagram of an alternative embodiment of a sensing device of a flow meter embodying the present invention similar to that shown in FIG. 1.

FIG. 6 shows another pitch and catch configuration for the sensing device 112 contemplated by the present invention. This configuration is similar to that shown in FIG. 5 except that the sensors disposed between the end sensors function as both a transmitter and a receiver. This pitch and catch configuration reduces the number of sensors needed to operate.

Referring back to FIG. 1, the signals $S_1(t)$-$S_N(t)$ received from each ultrasonic sensor 114, 116, 118 and 120 are processed by an ultrasonic signal processor 128 and a signal processor 130 (having an array processor 131) for determining the velocity of the fluid flow and/or volumetric flow rate. The signal processor 130 includes at least one of array processing logic, as will be described in greater detail hereinafter (See FIGS. 13 and 14); and cross-correlation processing logic, as also will be described in greater detail hereinafter (FIG. 15).

One should appreciate that the present invention is applicable to at least all the configurations of an ultrasonic flow meter considered herein (as well as others not described herein), and will be described in greater detail hereinafter. Specifically, the present invention teaches complimentary approaches to attenuating or eliminating the structural borne component 100 of the ultrasonic signal 102 (FIG. 8). For example, one embodiment comprises a structurally significant housing, a second embodiment including piezoelectric films applied to the outer surface of the pipe 104, and a third embodiment includes ring-around blocks affixed to the outer surface of the pipe 104, each embodiment directed to, as described herein, dampening the structural borne ultrasonic component.

A first embodiment, as shown in FIGS. 7A and 7B, involves the use of a structurally significant housing 132 to clamp-on to the outside of the process piping 104. The housing 132 is structurally significant in terms of mass and stiffness as compared to the pipe 104 itself and once the clamp-on ultrasonic meter 110 (see FIG. 1) (including the housing 132) is mounted to the pipe 104, the housing 132 and pipe 104 wall essentially form a single structural body at the ultrasonic excitation frequencies of interest. By clamping the structurally significant housing 132 to the pipe 104 with sufficient force, possibly with the addition of epoxy, the ultrasonic vibrational characteristics of the pipe 104 is effectively modified.

More specifically, the structurally significant housing 132 essentially modifies the structural properties of the entire structural path (or substantially the entire path) between the transmitting and the receiving ultrasonic transducers 122, 124. The structurally significant housing 132 contacts and reinforces all areas of the pipe 104 except for the immediate area of the transmitting and receiving transducers 122, 124 (defined below as area 103). Given that the flexural stiffness of a plate scales with the cube of the thickness of the plate, doubling the effective wall thickness increases the effective flexural stiffness by a factor of eight (8). Thus, as one rule of thumb, this invention considers doubling the flexural stiffness by at least two times as being "significant" and thus a structural housing 132 of the same material as the pipe 104 need only result in an about twenty-five percent (25%) increase in effective pipe 104 wall thickness to be considered significant. Accordingly, the present invention enhances the relative ability of the transmitting and receiving sensors 122, 124 to communicate with an ultrasonic signal through the fluid 126 by minimizing adverse effects of the structurally borne component 100 of the ultrasonic signal 102.

Figure 9A:
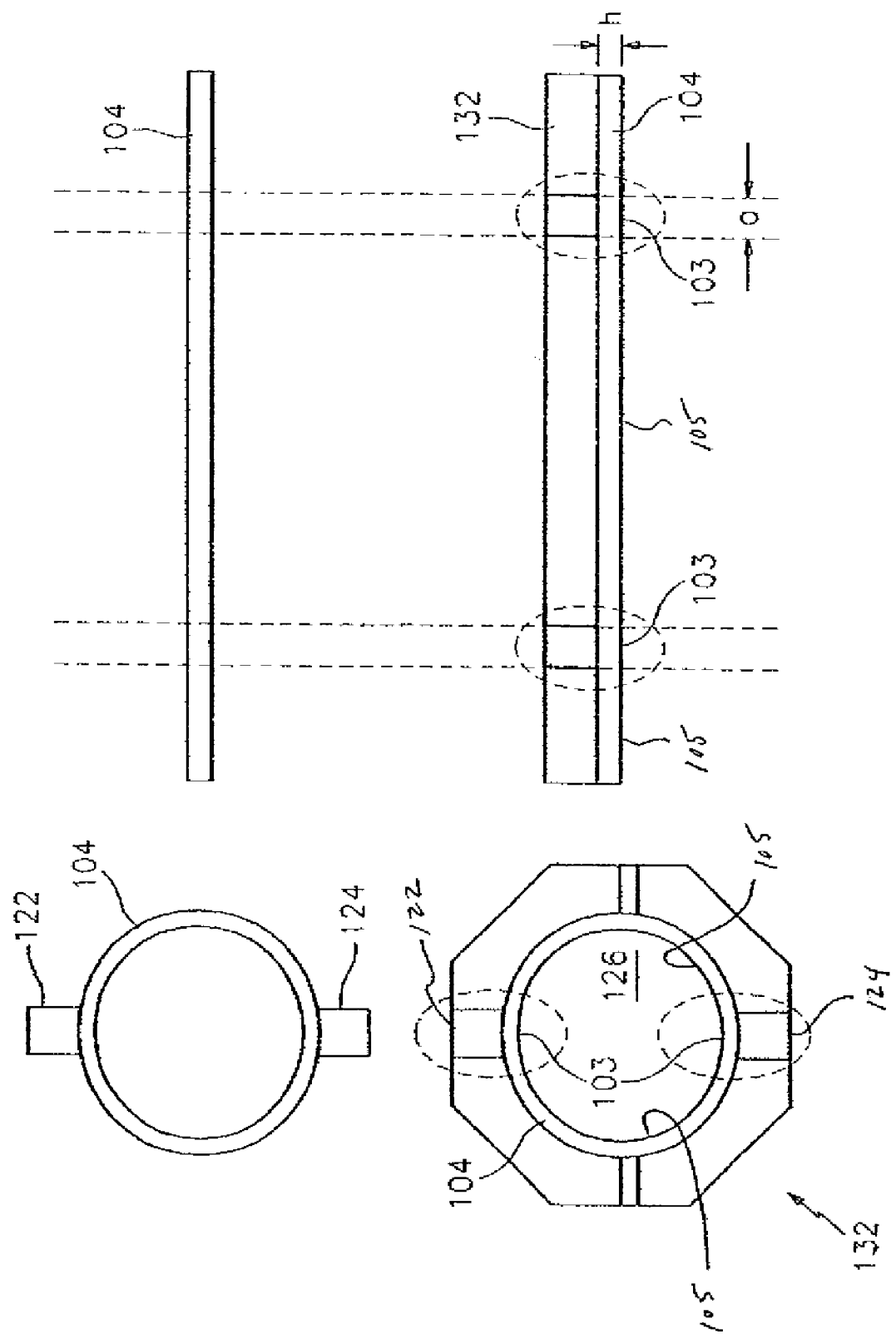
FIG. 9A is a cross-sectional view of wrapped and unwrapped pipe wall having a housing in accordance with the present invention and one embodiment having no housing.
Figure 12A:
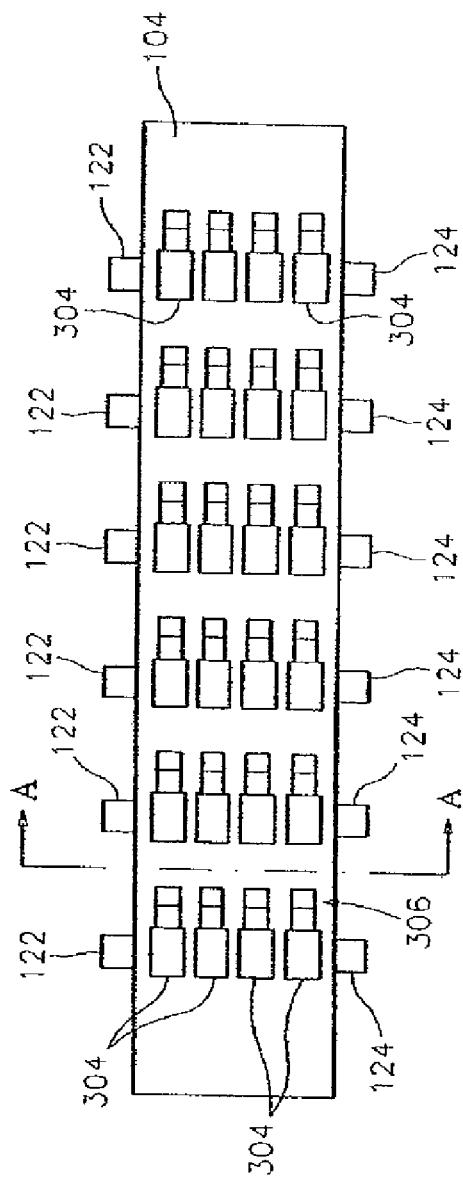
FIG. 12A is an elevational view and a cross-sectional view of another embodiment of the present invention having piezoelectric patches for damping structural borne ultrasonic signals in accordance with present invention.
Figure 12B:
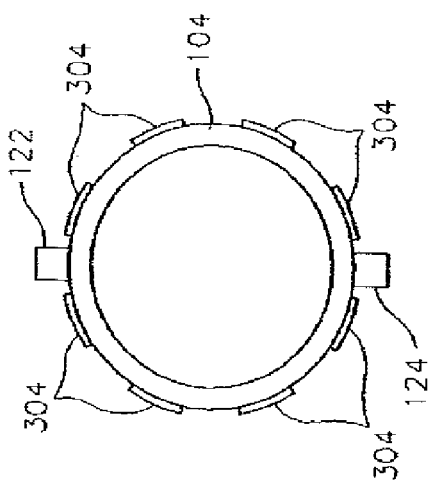
FIG. 12B is an elevational view and a cross-sectional view of the embodiment of FIG. 12A taken along line A-A.
Figure 12C:
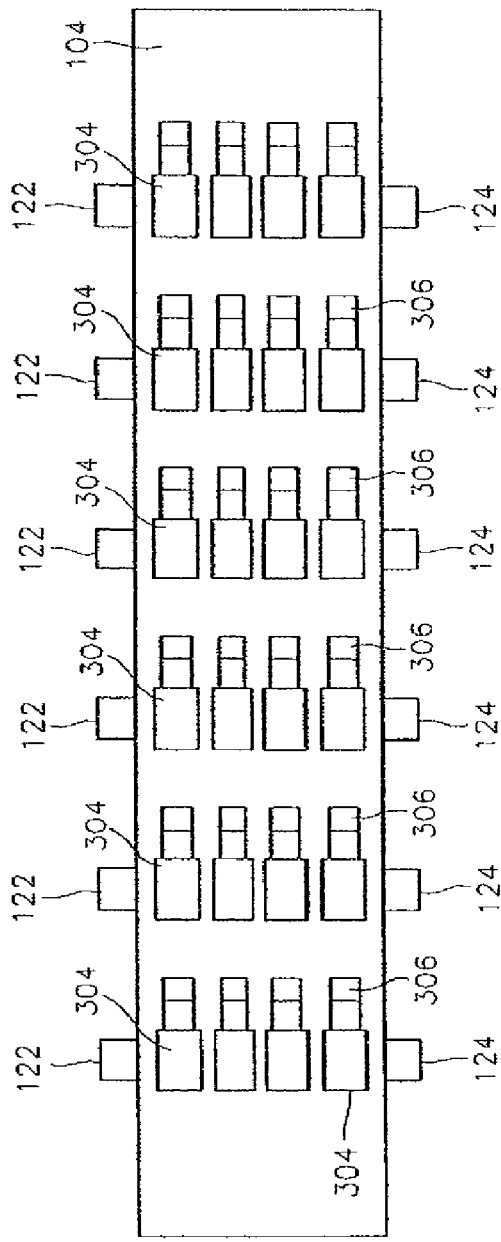
FIG. 12C is an elevational view and a cross-sectional view of the embodiment of FIG. 12A.
Figure 12D:
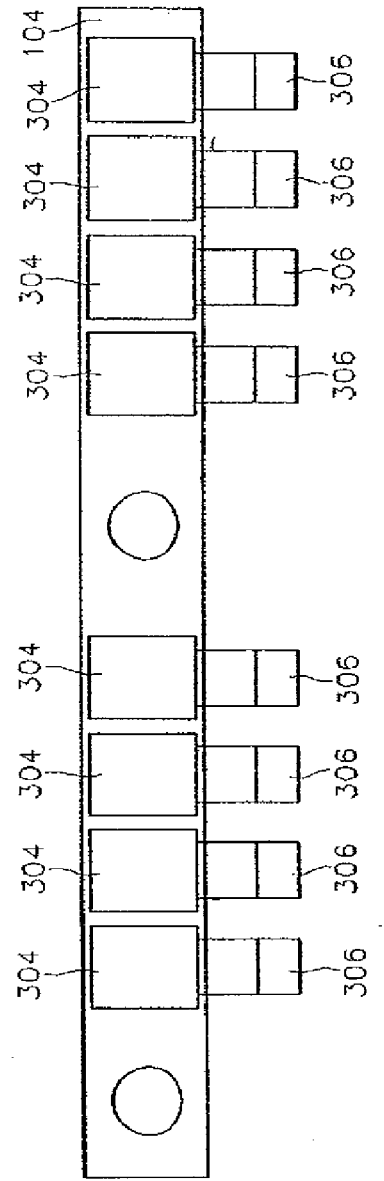
FIG. 12D is an elevational view and a cross-sectional view of the embodiment of FIG. 12A.

In addition to impeding the propagation of the structural wave component 100 from the transmitting sensor 122 to the receiving sensor 124, the design of the structurally significant housing 132 can be optimized to increase the transmission of fluid borne ultrasonic wave component 102. Referring to FIG. 9A, with the structurally significant housing 132 in place, an unreinforced area 103 of the pipe 104 wall in proximity to the sensors 122, 124 effectively appears as a clamped "diaphragm" in that the area 103 (e.g., having a diameter "a") about the sensors 122, 124 is more flexible than an area 105 reinforced by the housing 132.

Blevins, Formulas for Natural Frequency and Mode Shapes, (which is incorporated herein by reference) provides formulas for the natural frequency of a clamped diaphragm. For example, for a clamped diaphragm having a diameter, a, and thickness, h, for a material of modulus, E, Poisson ratio, v, and a mass per unit area, g, the natural frequency may be given by, $$f_{ij} = \frac{\lambda_{ij}^2}{2\pi a^2}\left[\frac{Eh^3}{12g(1-v^2)}\right]$$

where $f_{ij}$ is tabulated.

This formulation neglects the real world stiffening effect of the curvature of the pipe 104 wall in the unreinforced area 103 and thus will likely under predict the natural frequency for a given geometry. However, recognizing this limitation, initial calculations show that for a pipe 104 having a wall of about 0.3 inch, and unreinforced sensor areas 103 of roughly about 0.75 inch in diameters, a flat plate circular disk has resonant frequencies on the order of 10,000 Hz to 500,000 Hz, which is within the range of ultrasonic transducers. Thus, tuning the natural frequency of the diaphragm system 103 that is formed using a structurally significant housing 132 with the primary transmission frequency of the ultrasonic sensors 114, 116, 118 and 120—created by either driving the transducer at a specific frequency, or pulsing the transducer, is both practical and feasible with commonly available ultrasonic transducers and the design proposed herein.

The standard, unreinforced pipe does demonstrate frequency selectivity with respect to normal incidence ultrasonic waves. The transmission of normal incident ultrasonic waves 102 (FIG. 8) is maximized at frequencies that correspond to the wavelength of compression waves in the pipe 104 wall being an integral number of halfwave lengths, $$\lambda = \frac{2t}{n} \text{ or } f = n\frac{c}{2t},$$

Thus, for a 0.3 inch thick steel pipe, maximum transmission occurs at 340 KHz, 680 KHz, 1020 KHz, etc.

The effect of the structurally significant housing 132 would be maximized if the resonant frequency of the diaphragm system (e.g., areas 103 and 105) designed above coincided with one of the frequency of maximum transmission.

The design task of aligning the two resonant frequencies becomes one of selecting the diameter of the "diaphragm" (e.g., areas 103 versus 105) such that the natural frequency of the "diaphragm" lines up with the frequency of maximum transmission. Inspection of the above equations shows that this condition is essentially met for "diaphragms" with radii equal to the thickness of the pipe 104 wall.

Thus, under the simplified, but still realistic assumptions discussed herein, one optimal "diaphragm" diameter (diameter "a" of area 103) may be equal to two (2) times the thickness of the wall of the pipe 104. These values are tabulated in Table 1, shown in FIG. 9B. Note that as the pipe 104 wall gets thicker, the optimal diaphragm diameter "a" increases. Given the size of conventional transducers, this effect may be better leveraged for thick wall pipes, such as those used in high-pressure oil and gas wells.

Referring to FIGS. 10A and 10B, an additional embodiment of a structurally significant housing 200 is shown, wherein the presence of the structurally significant housing 200 provides multiple impedance changes, alternate energy dissipation paths, and augmented damping to reduce the level of structural borne noise 100 present to interfere with the fluid borne signal 102 required to make a flow measurement. Specifically, the structurally significant housing 200 includes viscoelastic damping material 202 introduced into slots 204 in the housing 200. For structural waves 100 propagating through the housing, the design of the slots 204 provide for shearing of the viscoelastic material 202, effectively augmenting the damping of the structural wave 100.

Referring to FIGS. 11A and 11B, another embodiment of a structurally significant housing 300 is shown with damping material 202 (e.g., viscoelastic damping material) attached between the housing 300 and structurally significant plates 302 (e.g., steel plates) affixed to the housing 300. The structurally significant housing 300 and the structurally significant plates 302 serve to constrain the viscoelastic material 202 when deflected, effectively augmenting the damping of the structural wave 100.

While the present invention of a structurally significant housing 132, 200, 300 attenuates the structural borne ultrasonic signals 100 propagating circumferentially around the pipe 104, one should appreciate that the housing 132, 200, 300 will also attenuate or eliminate axially propagating structural borne ultrasonic signals 100. Further, while the housing 132, 200, 300 is shown as a single housing comprised of two halves bolted together to retain the ultrasonic sensors 114, 116, 118 and 120 of the array of sensors 112, one should appreciate that the present invention contemplates that the ultrasonic meter may comprise a plurality of discreet independent structurally significant housings, wherein each sensor 114, 116, 118 and 120 of the array 112 may be mounted to the pipe 104 by a respective structurally significant housing 132, 200, 300. It is further contemplated that a housing 132, 200, 300 may also include any number of ultrasonic sensors 114, 116, 118 and 120 less than the total number of the array 112.

Referring to FIGS. 12A, 12B, 12C and 12D, an additional approach of attenuating or damping the structural borne ultrasonic signal or vibration 100 includes the use of piezo films 304 applied to the outer surface of the pipe 104. Piezo devices 304 bonded to a vibrating structure and electrically shunted to dissipate charge generated by deformation are well known to serve as effective dampening devices for structural vibration, for example, piezo damping of fan blades and the like. By tuning the electrical properties of a piezo RLC circuit 306, the circuit 306 can be optimized to preferentially damp structural vibration of a specific frequency.

One objective of the current invention is to bond piezoelectric materials (e.g. PVDF film) 304 to the pipe 104 wall along the region of the wall in which the interfering structural borne ultrasonic vibration 100 (see FIG. 8) would travel. The circuitry 306 could be broadband in nature or tuned to optimize attenuation of vibrations at specific frequencies.

Alternatively to the passive electronic system described above, the PVDF film 304 could also be used in an active circuit to preferentially damp out specific structural vibration. One piezoelectric film 304 contemplated in the present invention is similar to that shown in U.S. patent application Ser. No. 10/712,833, filed on Nov. 12, 2003, which is incorporated herein by reference.

In one configuration envisioned, the PVDF system is applied to the pipe 104 as a separate sub system of the existing ultrasonic flow metering system. Typical, piezo transducers are used to launch and detect ultrasonic signals. The proposed use of piezo dampers constitute a separate system designed to reduce or eliminate the structure borne component 100 of the ultrasonic signal, unintentionally generated as a by-product of generating the fluid borne component 102, arriving at the ultrasonic detector 124 ideally intended to respond to only fluid borne ultrasonic devices. An illustration of one embodiment of this concept is shown in FIGS. 12A, 12B, 12C and 12D.

The compressional wavelength in steel at 1 MHz is approximately 0.2 inch. Ideally, the spatial extent of the PVDF patches should target an odd integral number of half wavelengths, namely about 0.1, 0.3, 0.5 inch and the like.

Referring back to FIG. 1, the flow logic in the processor 130 may determine the velocity of each sensor in the array of sensors 114, 116, 118 and 120 using one or both of the following techniques to determine the convection velocity of vortical disturbances within the process flow 126 or other characteristics of the process flow 126 that moves/convects with the process flow 126 by: (1) characterizing the convective ridge of the vortical disturbances or other characteristics using array processing techniques that use an array 112 of ultrasonic sensors 114, 116, 118 and 120; and/or (2) cross-correlating unsteady variations in the ultrasonic signals using ultrasonic sensors 114, 116, 118 and 120. It should be appreciated that while the sensors 114, 116, 118 and 120 have been shown and described, the present invention is not limited in this regard and the number of sensors can vary. For example, any number of sensors may be used, such as two (2), three (3), four (4), . . . to sixteen (16) sensors, without departing from the scope of the invention.

Figure 13:
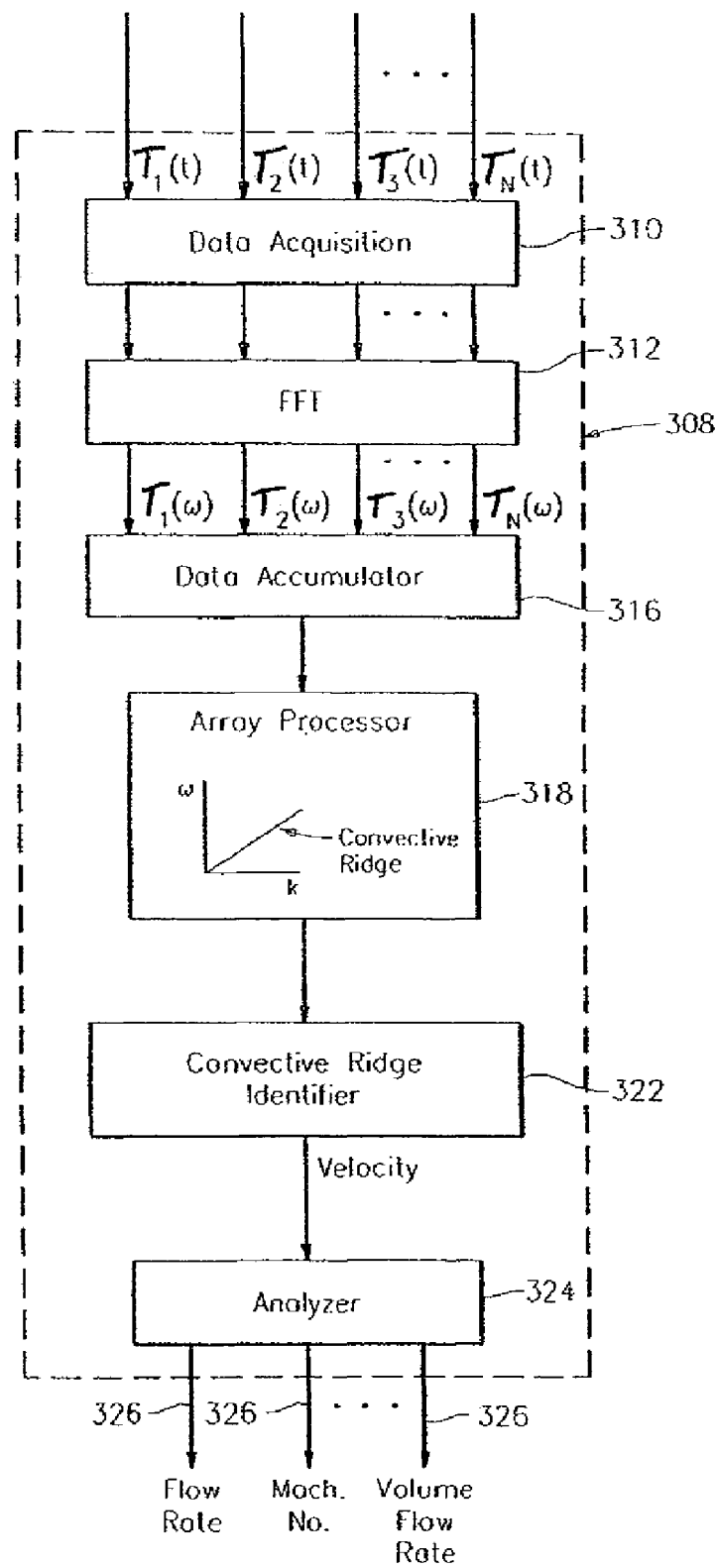
FIG. 13 is a block diagram of a flow logic used in the apparatus of the present invention.

Referring to FIG. 13, a block diagram illustrating the flow logic 308 in the processor 130 of FIG. 1 is shown and is used to characterize the convective ridge of the unsteady variations of the ultrasonic signals and determine the flow rates. As shown in FIG. 13, the flow logic 308 includes a data acquisition unit 310 (e.g., A/D converter) that converts the analog signals $T_1(t) \ldots T_N(t)$ to respective digital signals and provides the digital signals $T_1(t) \ldots T_N(t)$ to FFT logic 312. The FFT logic 312 calculates the Fourier transform of the digitized time-based input signals $T_1(t) \ldots T_N(t)$ and provides complex frequency domain (or frequency based) signals $T_1(\omega), T_2(\omega), T_3(\omega), \ldots T_N(\omega)$ indicative of the frequency content of the input signals. It should be appreciated that instead of FFTs, any other technique for obtaining the frequency domain characteristics of the signals $T_1(t)$-$T_N(t)$, may be used. For example, the cross-spectral density and the power spectral density may be used to form one or more frequency domain transfer functions (or frequency responses or ratios) discussed hereinafter.

One technique of determining the convection velocity of the coherent structures (e.g., turbulent eddies) 314 within the flow 126 (FIG. 2) is by characterizing a convective ridge of the resulting unsteady variations using an array 112 of sensors 114, 116, 118 and 120 or other beam forming techniques, similar to that described in U.S. patent application Ser. No. 09/729,994, filed Dec. 4, 2000, now U.S. Pat. No. 6,609,069, which is incorporated herein by reference in its entirety.

A data accumulator 316 accumulates the frequency signals $T_1(\omega)$-$T_N(\omega)$ over a sampling interval, and provides the data to an array processor 318, which performs a spatial-temporal (two-dimensional) transform of the sensor data, from the x-t domain to the k-ω domain, and then calculates the power in the k-ω plane, as represented by a k-ω plot.

The array processor 318 may use standard so-called beam forming, array processing, or adaptive array-processing algorithms, i.e. algorithms for processing the sensor signals using various delays and weighing to create suitable phase relationships between the signals provided by the different sensors, thereby creating phased antenna array functionality. In other words, the beam forming or array processing algorithms transform the time domain signals from the sensor array 112 into their spatial and temporal frequency components, i.e. into a set of wave numbers given by $k=2\pi/\lambda$, where $\lambda$ is the wavelength of a spectral component, and corresponding angular frequencies given by $\omega=2\pi\nu$.

It should be appreciated that the prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use, or combined use, of other adaptive array processing algorithms, such as MUSIC algorithm. The present invention also recognizes that such techniques can be used to determine flow rate, i.e. that the signals caused by a stochastic parameter convecting with a flow 126 are time stationary and may have a coherence length long enough so that it is practical to locate sensors 114, 116, 118 and 120 apart from each other and yet still be within the coherence length.

Convective characteristics or parameters have a dispersion relationship that can be approximated by the straight-line equation, $$k=\omega/u,$$

where u is the convection velocity (flow velocity).

Figure 14:
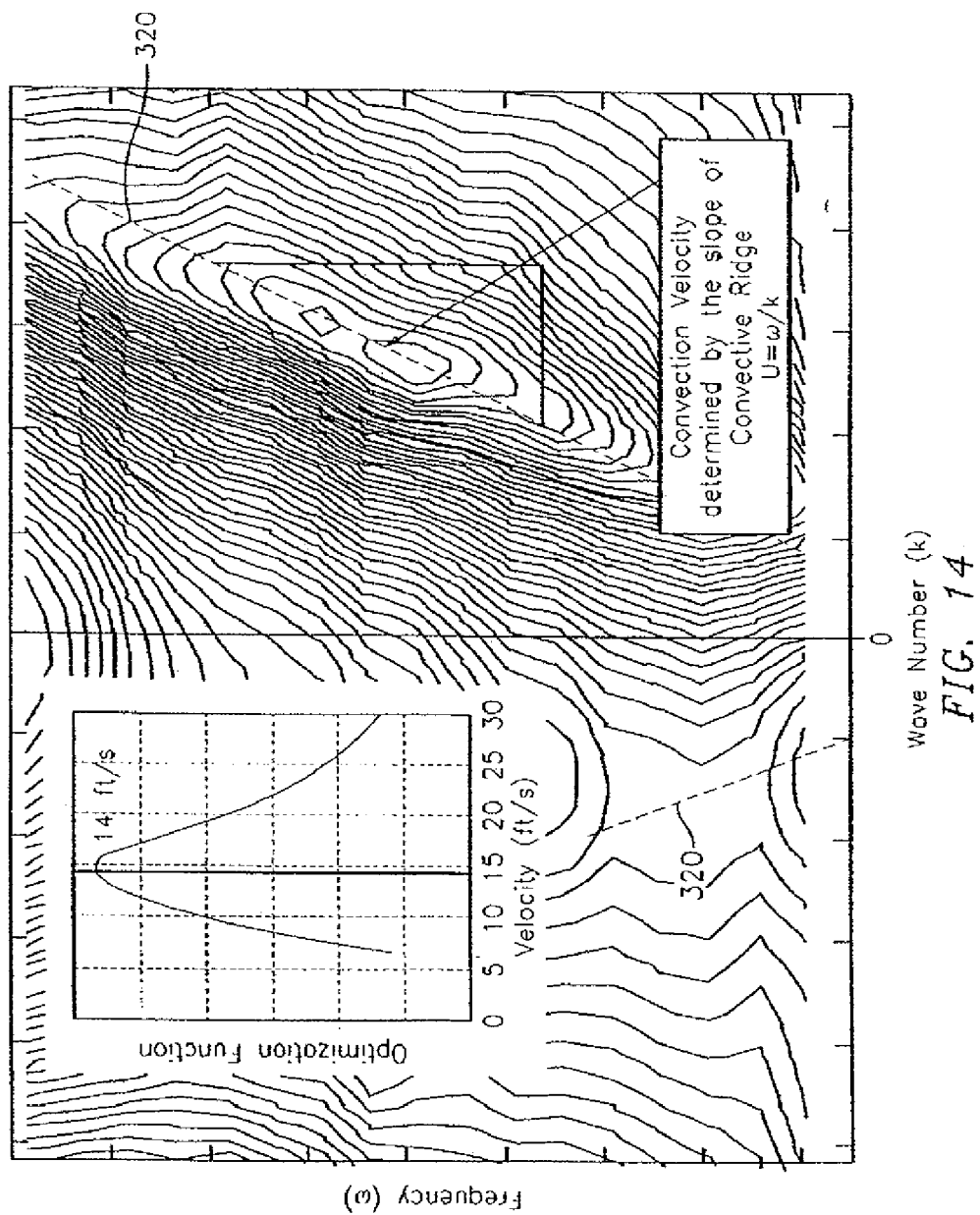
FIG. 14 is a k-ω plot of data processed from an apparatus embodying the present invention that illustrates slope of the convective ridge, and a plot of the optimization function of the convective ridge.
Figure 15:
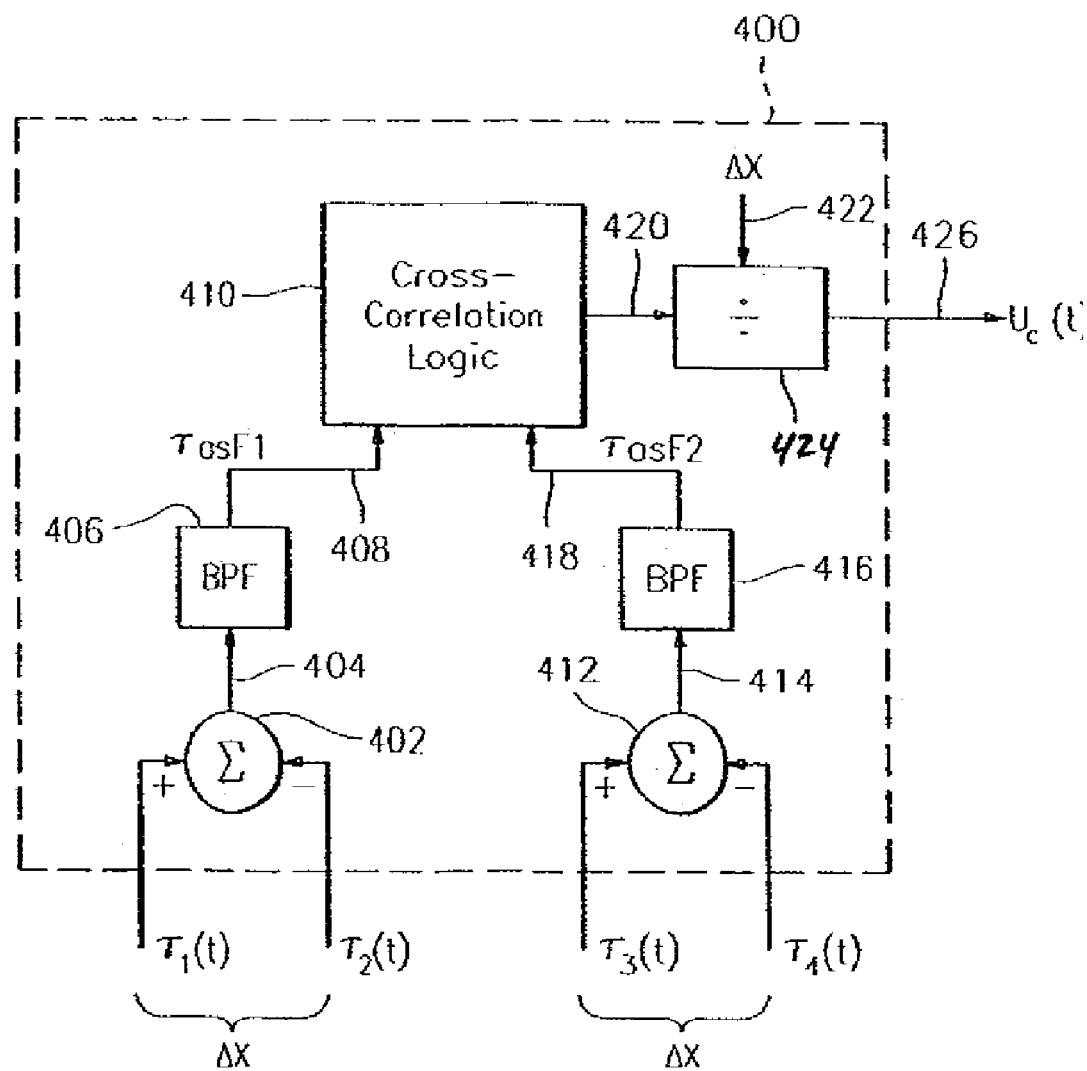
FIG. 15 is a block diagram of an apparatus for measuring the vortical field or other flow characteristics of a process flow within a pipe, in accordance with the present invention.

Referring to FIG. 14, a k-ω plot is a plot of k-ω pairs obtained from a spectral analysis of sensor samples associated with convective parameters that are portrayed so that the energy of the disturbance spectrally corresponds to pairings that might be described as a substantially straight ridge, wherein the ridge, in turbulent boundary layer theory, is called a convective ridge.

To calculate the power in the k-ω plane, as represented by a k-ω plot (see FIG. 14) of either of the signals, the array processor 318 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensors 114, 116, 118 and 120.

The present embodiment may use temporal and spatial filtering to precondition the signals to effectively filter out the common mode characteristics and other long wavelength (compared to the sensor spacing) characteristics in the pipe 104 by differencing adjacent sensors 114, 116, 118 and 120 and retaining a substantial portion of the stochastic parameter associated with the flow field and any other short wavelength (compared to the sensor spacing) low frequency stochastic parameters.

In the case of suitable coherent structures 314 being present, the power in the k-ω plane shown in the k-ω plot of FIG. 14 shows a convective ridge 320. The convective ridge 320 represents the concentration of a stochastic parameter that convects with the flow 126 and is a mathematical manifestation of the relationship between the spatial variations and temporal variations described above. Such a plot will indicate a tendency for k-ω pairs to appear more or less along a line 320 with some slope, wherein the slope indicates the flow velocity.

Once the power in the k-ω plane is determined, a convective ridge identifier 322 (FIG. 13) uses one or another feature extraction method to determine the location and orientation (slope) of any convective ridge 320 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 322 provides information about the different trial convection velocities, information referred to generally as convective ridge information.

An analyzer 324 examines the convective ridge information including the convective ridge orientation (slope). Assuming the straight-line dispersion relation given by $k=\omega/u$, the analyzer 324 determines the flow velocity and/or volumetric flow, which are output as parameters 326. The volumetric flow is determined by multiplying the cross-sectional area of the inside of the pipe 104 with the velocity of the process flow 126.

As previously noted, for turbulent Newtonian fluids, there is typically not a significant amount of dispersion over a wide range of wavelength-to-diameter ratios. As a result, the convective ridge 320 in the k-ω plot is substantially straight over a wide frequency range and, accordingly, there is a wide frequency range for which the straight-line dispersion relation given by $k=\omega/u$ provides accurate flow velocity measurements.

For stratified flows, however, some degree of dispersion exists such that coherent structures 314 convect at velocities which depend on their size. As a result of increasing levels of dispersion, the convective ridge 320 in the k-ω plot becomes increasingly non-linear.

Another technique for determining convection velocity of the coherent structures 314 within the flow 126 is by cross-correlating unsteady pressure variations using an array of unsteady pressure sensors.

Referring to FIG. 15, a processor 400 is provided which uses cross-correlation of unsteady variations of the ultrasonic signals to determine the flow rates. The processing unit 400 of FIG. 15 determines the convection velocity of the vortical disturbances within the flow 126 by cross correlating unsteady ultrasonic variations using an array of ultrasonic sensors 114, 116, 118 and 120, similar to that shown in U.S. Pat. No. 6,889,562, filed Nov. 8, 2001, which is incorporated herein by reference.

Referring to FIG. 15, the processing unit 400 has two measurement regions located a distance $\Delta X$ apart along the pipe 104. Each pair of sensors 114, 116 and 118, 120 of each region act as spatial filters to remove certain acoustic signals from the unsteady pressure signals, and the distances $X_1$, $X_2$ are determined by the desired filtering characteristic for each spatial filter, as discussed hereinafter.

In particular, in the processing unit 400, the ultrasonic signal $T_1(t)$ is provided to a positive input of a summer 402 and the ultrasonic signal $T_2(t)$ is provided to a negative input of the summer 402. The output of the summer 402 is provided to line 404 indicative of the difference between the two ultrasonic signals $T_1$, $T_2$ (e.g., $T_1-T_2=T_{as1}$).

The line 404 is fed to a bandpass filter 406, which passes a predetermined passband of frequencies and attenuates frequencies outside the passband. In accordance with the present invention, the passband of the filter 406 may be set to filter out (or attenuate) the dc portion and the high frequency portion of the input signals and to pass the frequencies therebetween. Other passbands may be used in other embodiments, if desired. Bandpass filter 406 provides a filtered signal $T_{asf1}$ on a line 408 to Cross-Correlation Logic 410, described hereinafter.

The ultrasonic signal $T_3(t)$ is provided to a positive input of a summer 412 and the ultrasonic signal $T_4(t)$ is provided to a negative input of the summer 412. The output of the summer 412 is provided on a line 414 indicative of the difference between the two ultrasonic signals $T_3$, $T_4$ (e.g., $T_3-T_4=T_{as2}$). The line 414 is fed to a bandpass filter 416, similar to the bandpass filter 406 discussed hereinbefore, which passes frequencies within the passband and attenuates frequencies outside the passband. The filter 416 provides a filtered signal $T_{asf2}$ on a line 418 to the Cross-Correlation Logic 410. The signs on the summers 402, 412 may be swapped if desired, provided the signs of both summers are swapped together. In addition, the ultrasonic signals $T_1$, $T_2$, $T_3$, $T_4$ may be scaled prior to presentation to the summers 402, 412.

The Cross-Correlation Logic 410 calculates a known time domain cross-correlation between the signals $T_{asf1}$ and $T_{asf2}$ on the lines 408, 418, respectively, and provides an output signal on a line 420 indicative of the time delay $\tau$ it takes for an vortical flow field 314 (or vortex, stochastic, or vortical structure, field, disturbance or perturbation within the flow) to propagate from one sensing region to the other sensing region. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field 314 also has a stochastic or vortical pressure disturbance associated with it. In general, the vortical flow disturbances 314 are distributed throughout the flow, particularly in high shear regions, such as boundary layers (e.g., along the inner wall of the pipe 104) and are shown herein as discrete vortical flow fields 314. Because the vortical flow fields (and the associated pressure disturbance) convect at or near the mean flow velocity, the propagation time delay $\tau$ is related to the velocity of the flow by the distance $\Delta X$ between the measurement regions, as discussed hereinafter.

Referring to FIG. 15, a spacing signal $\Delta X$ on a line 422 indicative of the distance $\Delta X$ between the sensing regions is divided by the time delay signal $\tau$ on the line 420 by a divider 424 which provides an output signal on the line 426 indicative of the convection velocity $U_c(t)$ of the saturated vapor/liquid mixture flowing in the pipe 104, which is related to (or proportional to or approximately equal to) the average (or mean) flow velocity $U_f(t)$ of the flow 126, as defined below:

$$U_c(t)=\Delta X/\tau \propto U_f(t)$$

The present invention uses temporal and spatial filtering to precondition the ultrasonic signals to effectively filter out the acoustic disturbances $P_{acoustic}$ and other long wavelength (compared to the sensor spacing) disturbances in the pipe 104 at the two sensing regions and retain a substantial portion of the ultrasonic signal $T_{vortical}$ associated with the vortical flow field 314 and any other short wavelength (compared to the sensor spacing) low frequency pressure disturbances $T_{other}$. In accordance with the present invention, if the low frequency pressure disturbances $T_{other}$ are small, they will not substantially impair the measurement accuracy of $T_{vortical}$.

While the cross-correlation was shown using four sensors, whereby two sensors were summed together to form a sensing region, the invention contemplates that each sensing region may only be comprised of one (or more) sensors disposed at an axial location along the pipe 104.

As mentioned hereinbefore, the present invention contemplates that the housing and blocks for attenuating the structural ultrasonic signals may be used with any configuration of ultrasonic sensors 114, 116, 118 and 120. Specifically any of the three classes of flow meters that utilize ultrasonic transducers, which include transit time ultrasonic flow meters (TTUF), doppler ultrasonic flow meters (DUF), and cross correlation ultrasonic flow meters (CCUF).

CCUF's measure the time required for ultrasonic beams to transit across a flow path at two, axially displaced locations along a pipe 104. Within this measurement principle, variations in transit time are assumed to correlate with properties that convect with the flow 126, such as vortical structure, inhomogenities in flow composition, temperature variations to name a few.

CCUF's utilize high frequency acoustic signals, i.e. ultrasonics, to measure much lower frequencies, time varying properties of structures in the flow 126. Like all other cross correlation based flow meters, the physical disturbances which cause the transit time variations should retain some level of coherence over the distance between the two sensors.

Cross correlation ultrasonic flow meters have been around since the early 1960's. CCUF's are typically much more robust to variations in fluid composition than the other ultrasonic-based flow measurement approaches such as transit time and Doppler based methods.

Although CCFU's are operationally more robust than other ultrasonic interpretation techniques, they suffer from drawbacks attributed to most cross correlation flow meters, i.e., they are have slow update rates and relatively inaccurate.

Transit time, defined as the time required for an ultrasonic beam to propagate a given distance, can be measured using a radially aligned ultrasonic transmitter and receiver. For a homogenous fluid with no transverse velocity components flowing in an infinitely rigid tube, the transit time may be given by the following relation:

$$t=D/A_{mix}$$

where t is the transit time, D is the diameter of the pipe 104, and $A_{mix}$ is the speed of sound propagating through the fluid 126.

In such a flow, variation in transit time is analogous to a variation in sound speed of the fluid. In real fluids however, there are many mechanisms, which could cause small variations in transit time which remain spatially coherent for several pipe diameters. For single phase flows, variations in the transverse velocity component will cause variations in transit time. Variations in the thermophysical properties of a fluid such as temperature or composition will also cause variations. Many of these effects convect with the flow. Thus, influence of transverse velocity of the fluid associated with coherent vortical structures 314 on the transit time enables transit time based measurements to be suitable for cross correlation flow measurement for flows with uniform composition properties. The combination of sensitivity to velocity field perturbation and to composition changes make transit time measurement well suited for both single and multiphase applications.

Despite CCUF's functioning over a wide range of flow composition, standard transit time ultrasonic flow meters (TTUF) are more widely used. TTUF's tend to require relatively well behaved fluids (i.e. single phase fluids) and well-defined coupling between the transducer and the fluid itself. TTUF's rely on transmitting and receiving ultrasonic signals that have some component of their propagation in line with the flow. While this requirement does not pose a significant issue for in-line, wetted transducer TTUF's, it does pose a challenge for clamp-on devices by introducing the ratio of sound speed in the pipe to the fluid as an important operating parameter. The influence of this parameter leads to reliability and accuracy problems with clamp-on TTUF's.

CCFU's, utilize ultrasonic transducers to launch and detect ultrasonic waves propagating normal to the flow path. Refraction of ultrasonic waves at the pipe/fluid interface is not an issue and the ratio between sound speed of pipe and the fluid does not direct effect operability.

In still another embodiment, each pair of transducers 114, 116, 118 and 120 comprise a single transmitter 122 to emit an ultrasonic signal through the flow 126 and a receiver, 124 which receives the respective signal for processing. The time it takes for the signal to arrive at the receiver transducer 124 for each pair is calculated and fed to the SONAR algorithms (in the array processor 131) where the flow rate is calculated. One embodiment uses a very simplistic signal detection algorithm that looks for a peak in the reading obtained from the receiver 124. This algorithm works well when a good signal-to-noise ratio is observed at the receiver 124, however when bubbles intersect the signal path between the transmitter 122 and receiver 124 a significant attenuation can occur, which will severely degrade the received signal quality. The amount of attenuation will vary depending on the bubble characteristics such as size and density.

Figure 16:
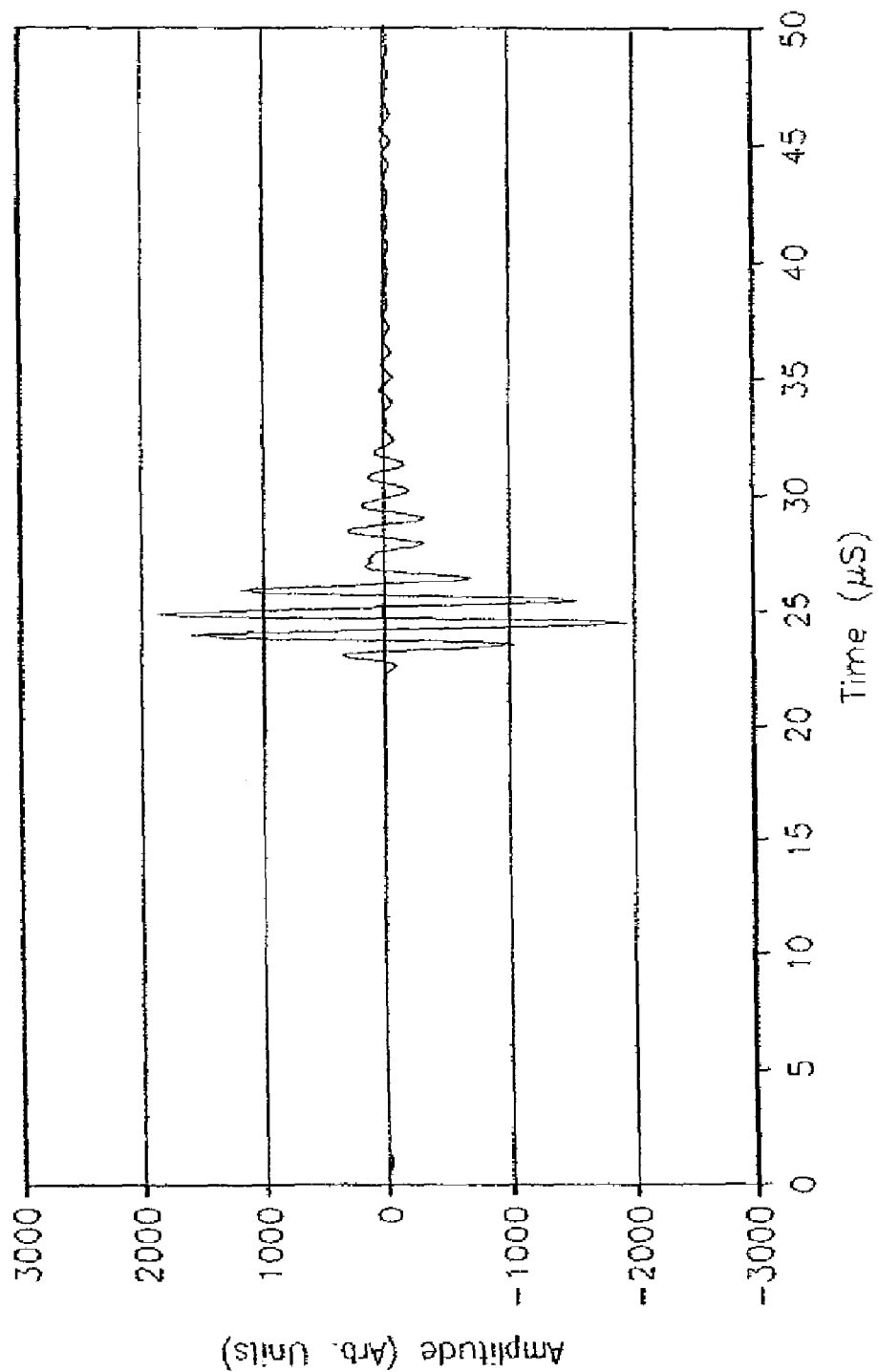
FIG. 16 is a plot of a signal created by a 1 MHz ultrasonic signal transducer, in accordance with the present invention.
Figure 17:
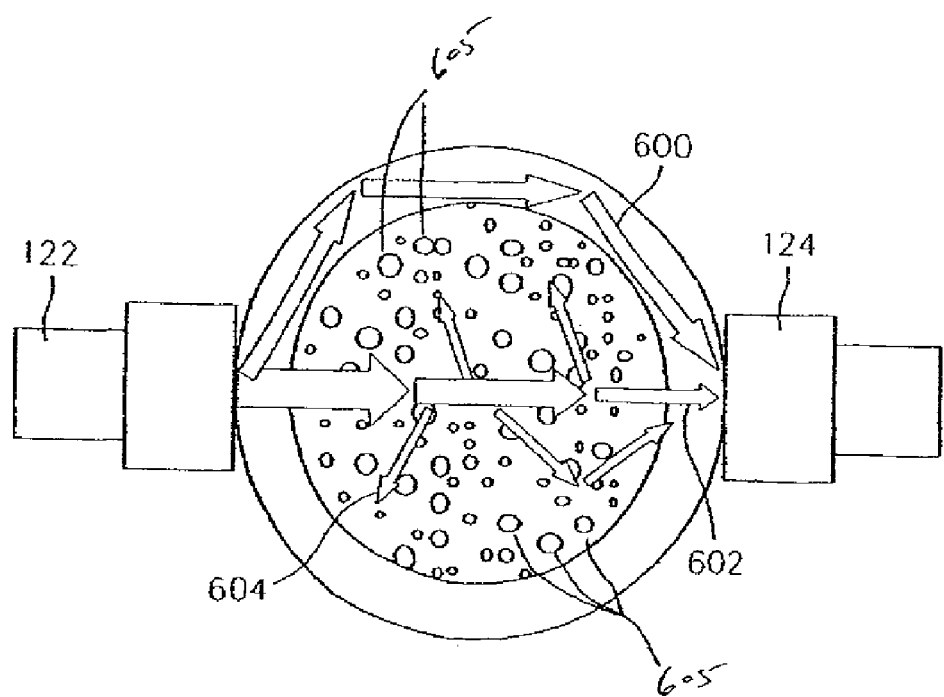
FIG. 17 is a cross-sectional view of structurally borne and fluid borne components propagating through a pipe wall having an ultrasonic sensor attached thereto.

Referring to FIG. 17, the transmitting ultrasonic transducer array 122 is periodically pulsed to create the ultrasonic signal that transmits through the pipe 104 and fluid. Each transducer will have a fundamental oscillation frequency, which when pulsed will emit a short ultrasonic burst signal. FIG. 16 shows the signal created by a 1 MHz ultrasonic transducer when pulsed with a ten nanosecond (10 ns) width pulse created in the flow meter 110. In typical applications the receiving ultrasonic transducer 124, located on the opposite side of a pipe 104, will receive this signal once it has bisected the pipe 104 however in addition to this primary through-transmitted signal other unwanted secondary signals will also be detected. These secondary signals include portions of the original signal that have been refracted or reflected along a different path through the pipe 104 than the preferred direct transmission. Often these secondary signals possess sufficient strength to still reach the receiver transducer 124 and will interfere with the desired signal. Examples of these secondary signals include the ring-around signals 600 that travel within the pipe wall 104, reflected signals 604 that may bounce off multiple interfaces such as the transducer-pipe interface or the pipe-liquid interface, or as in the case here where an array of transducers are used, from an adjacent transducer, as shown in FIG. 17.

Figure 18:
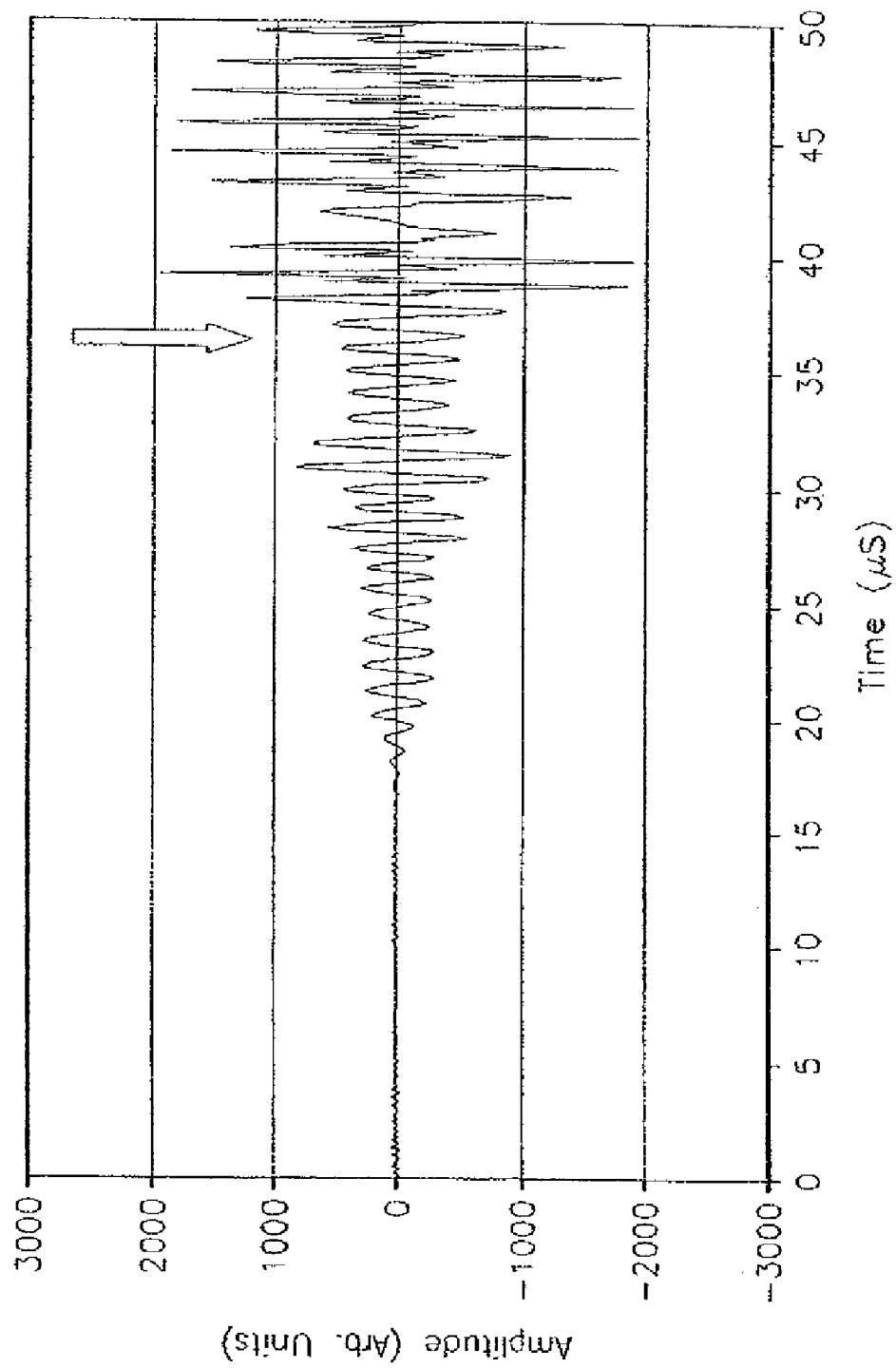
FIG. 18 is a plot of a received ultrasonic signal along with an unwanted ring-around signal, in accordance with the present invention.
Figure 19:
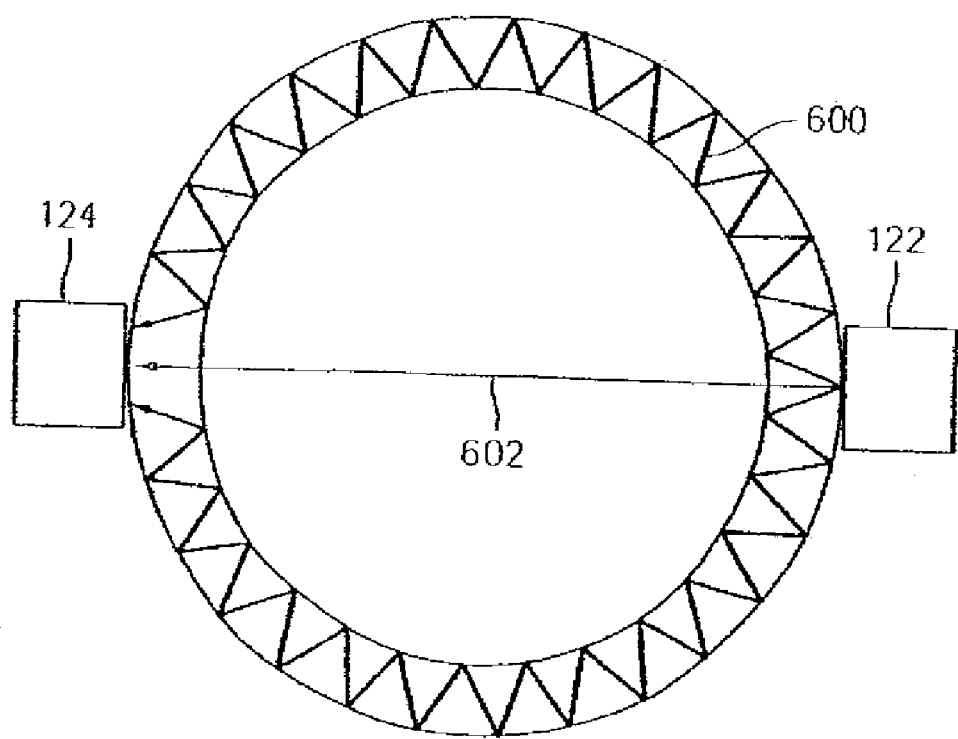
FIG. 19 is a cross-sectional view of structurally borne and fluid borne components propagating through a pipe wall having an ultrasonic sensor attached thereto.

The dominant secondary signal is the 'ring-around' signal 600. This is the portion of the ultrasonic signal that travels around through the wall of the pipe 104 and can still be detected by the receiving transducer 124. FIG. 18 shows a diagram of this signal as compared to the through-transmitted signal 602. As shown in FIG. 19, ultrasonic transmitting and receiving transmitters 122, 124, respectively, are shown attached to the outer surface of a pipe 104. They are arranged such that the generated ultrasonic signal will be normal to the direction of the fluid flow and travel through the center 602 of the liquid within the pipe 104. As discussed above, as the ultrasonic signal travels through the pipe 104, bubbles 605 (FIG. 17) and other matter within the pipe 104 will scatter and attenuate the signal (e.g., form signals 604) before it fully traverses the pipe 104 and is detected by the receiving transducer 124. Also depicted is the 'ring-around' signal 600. This signal is created through reflection and diffraction between the transmitting ultrasonic transducer 122, the pipe wall 104 and the material present inside the pipe 104 due to the large impedance mismatch between the various materials. As an example, the impedance of steel such as, for example, in steel piping, is 45 MRayls in contrast to fluid which has an impedance of 1.5 MRayls. In this case, only a small percentage of the ultrasonic signal is actually injected into the fluid while the rest is reflected throughout the overall system. The majority of this excess energy is present in the pipe 104 wall in the form of shear and compressional ultrasonic waves 600. These waves will travel throughout the pipe 104 and will be seen by the receiving transducer 124 along with any desired signals 602. Coupled with the fact that the through-transmitted signal 602 can be significantly attenuated (e.g., signals 604) as it travels through the fluid 126 in the pipe 104, it can be very difficult to distinguish the wanted signal from all the secondary signals. FIG. 19 shows an example of a received ultrasonic signal 602 along with an unwanted 'ring-around' signal 600. The arrow indicates the location of the through-transmitted pulse in relation to the large 'ring-around' signal. Contrast the attenuated ultrasonic signal in FIG. 18 to the clean ultrasonic signal seen in FIG. 16.

To increase the system robustness of the ultrasonic flow meter 110, the amount of the noise signal may be decreased by mechanically reducing the strength of the secondary ring-around ultrasonic signals that were able to reach the detectors.

Signal to Noise

It should be appreciated that the quality of any flow measurement, independent of the technology, is typically dependent upon the signal to noise ratio (S/N). Noise, in this case, is defined as any portion of the measured signal that contains no flow information. It is desirable to maximize the S/N to obtain optimum performance. As mentioned, the dominant noise source for the ultrasonic flow meter 110 was determined to be ring-around noise. Ring-around noise is defined as the signal (signal 100) seen by the receiving transducer 124 that has not passed through the fluid 126, but instead traveled via the pipe 104 wall. This signal 100, 600 contains no flow information and, in certain cases, can corrupt the measurement of the signal 102, 602 that has passed through the fluid 126. FIG. 19 shows both the signal path and ring-around path.

The ultrasonic flow meter 110 measures the modulation of the time-of-flight (TOF) measurement orthogonal to the flow direction. The TOF modulation is due to the vortical disturbances in the beam path and the flow velocity is determined by correlating these coherent modulations over the length of the sensor array.

Under ideal conditions, the ratio of the signal passing through the fluid 126 to the ring-around noise is high, and/or the differential TOF between the signals is large, and a flow measurement can be made. In situations where the straight through signal is attenuated due to properties of the fluid 124 (air bubbles, particulates, etc.) the S/N ratio can be substantially reduced and the flow measurement compromised. In cases where the signal and noise temporally overlap, and/or in situations where the ring-around signal is greater than the straight through signal, advanced signal processing algorithms need to be employed to detect the signal. In order to reduce the burden placed on the detection algorithm to detect small signals in the presence of a large ring-around signal, methods of reducing the amplitude of the ring-around noise were investigated.

Figure 20:
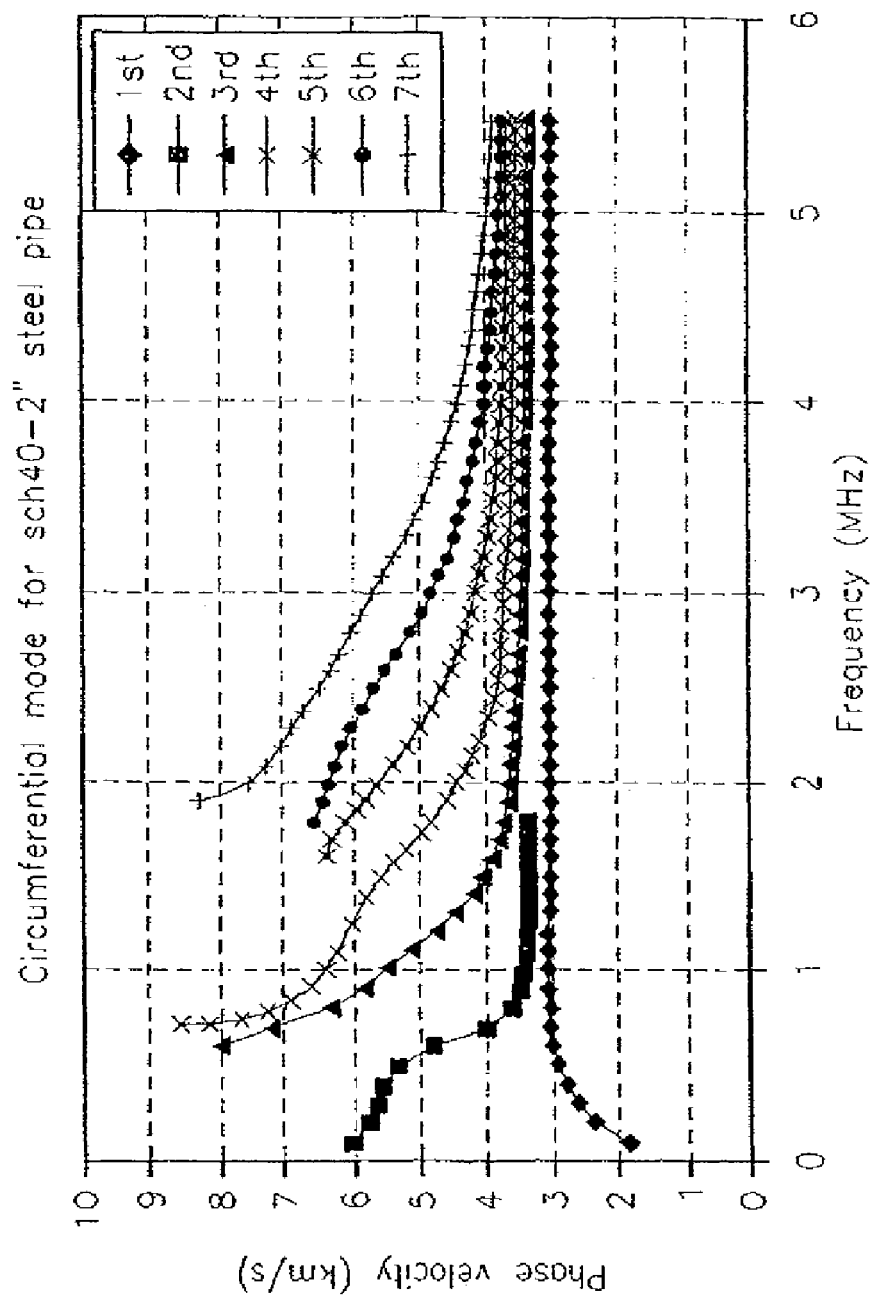
FIG. 20 is a plot showing the phase velocity of supported circumferential modes with the wall of a pipe, in accordance with the present invention.

The properties of the ring-around energy differ depending upon the wall thickness of the pipe 104, transducer frequency, pipe surface quality, and transducer size. Generally speaking, higher levels of ring-around are seen at smaller pipe diameters (e.g., about two (2) inches) for a given transducer excitation frequency due to the tighter curvature of the wall. Ring-around signals can be generated when energy from the transducer is either directly coupled into the pipe wall and/or be a result of reflected energy from the inner pipe/liquid interface. This energy can propagate as a variety of different waves, such as shear, longitudinal and surface waves. FIG. 20 shows the phase velocity of supported circumferential modes within the wall of a schedule 40, 2 inch steel pipe. It can be seen that at low excitation frequencies, such as 1 MHz, four modes can be supported in the pipe wall, wherein the number of modes capable of being supported increases with increased frequency. The phase velocity of the lower order modes converges to approximately 3000 meters/sec.

Figure 21:
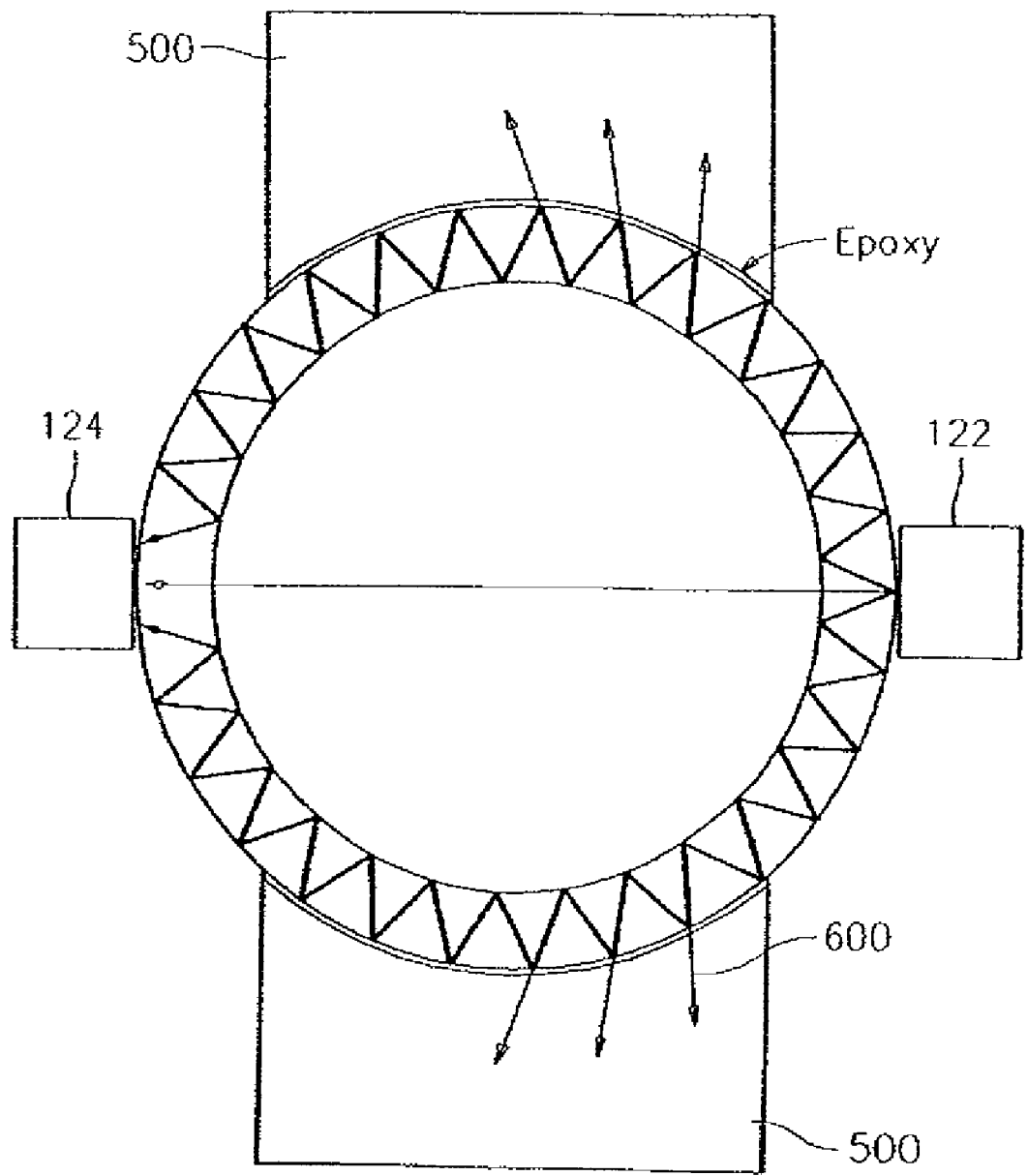
FIG. 21 is a cross-sectional view of structurally borne and fluid borne components propagating through a pipe wall having an ultrasonic sensor attached thereto and having a pair of blocks affixed to the pipe wall to attenuate the ring-around signal, in accordance with the present invention.

One approach to eliminate ring-around involves coupling the energy into a mechanical structure attached to the pipe 104. Referring to FIG. 21, two blocks 500 (e.g., steel blocks) were machined with a curvature slightly larger than the radius of a two inch (2 in) pipe 104. Acoustic coupling gel was applied between the pipe 104 and the curved face of the blocks 500. The blocks 500 were then coupled to the pipe 104 which was then filled with water and the ring-around noise was measured and compared to the straight through signal. This was accomplished by first measuring and recording the received signal containing both the ring-around noise and the straight through signal, followed by a measurement with the straight through beam blocked. The difference between the measurements represents the contribution of the ring-around noise. The results of these tests showed the blocks had little impact on the attenuation of the acoustic energy propagating in the pipe 104 wall.

Figure 22:
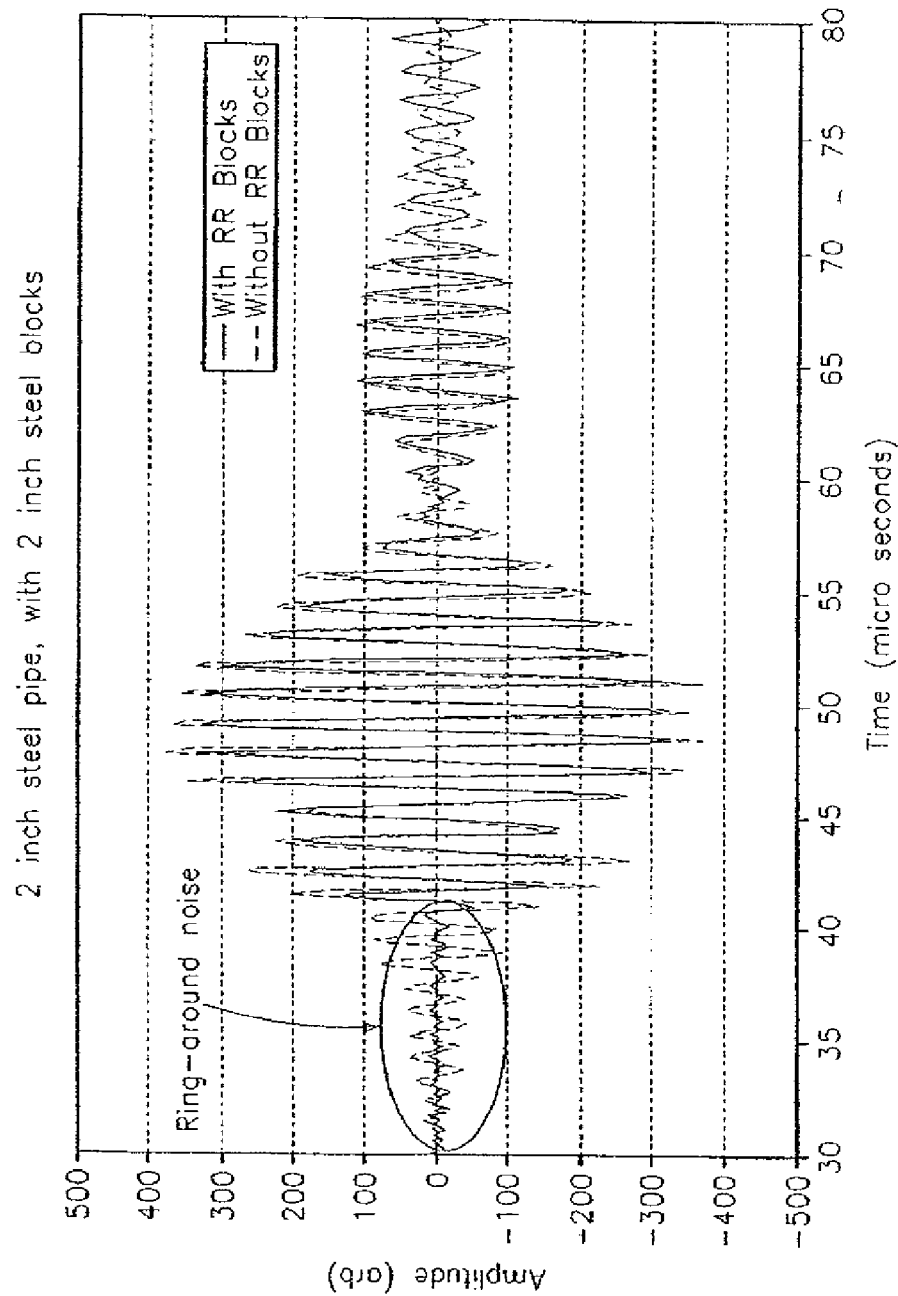
FIG. 22 is a plot showing the received signal with and without ring-around blocks affixed to the pipe wall.

A second test was conducted where the blocks 500 were affixed to the pipe 104 wall with an adhesive such as, for example, an epoxy. Comparison of these measurements showed substantial attenuation of the ring-around energy. FIG. 22 shows the received signal with and without epoxied ring-around blocks 500. The first arrival signal without ring-around blocks occurs at approximately thirty-one micro seconds (31 μsecs). This is consistence with the calculated transit time through steel. The straight through signal containing the flow information has a transit time of forty-one micro seconds (41 μsec). Ring-around blocks attenuate the ring-around noise resulting in an improved signal to noise at the receiver 124. It should be appreciated that improvements in S/N of up to twenty decibels (20 dB) were realized with ring-around blocks.

It should also be appreciated that while the present invention contemplates using a block of material 500 (e.g., steel) attached or engaged to the pipe 104 to attenuate acoustic waves propagating through the pipe 104 wall, the invention further contemplates that the blocks 500 may be comprised of a sheet of material (e.g., steel, tin and lead) that is affixed with epoxy or otherwise engaged or attached to the pipe 104 wall. The sheet material may cover a substantial portion of the circumference and length of the array of sensors 114, 116, 118 and 120. The attenuation design may comprise of a plurality of respective sheets for each ultrasonic sensor pair and disposed on both sides of the pipe 104 between the sensor pair.

Figure 23:
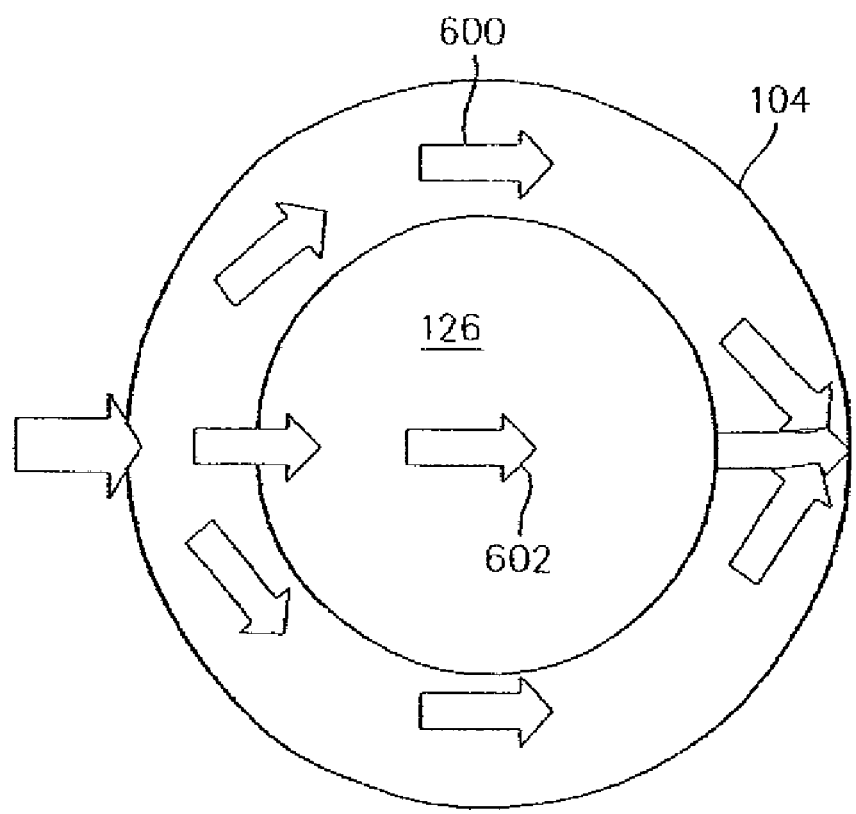
FIG. 23 is a diagram illustrating the flow of ultrasonic energy injected into a pipe without ring-around reducing blocks.
Figure 24:
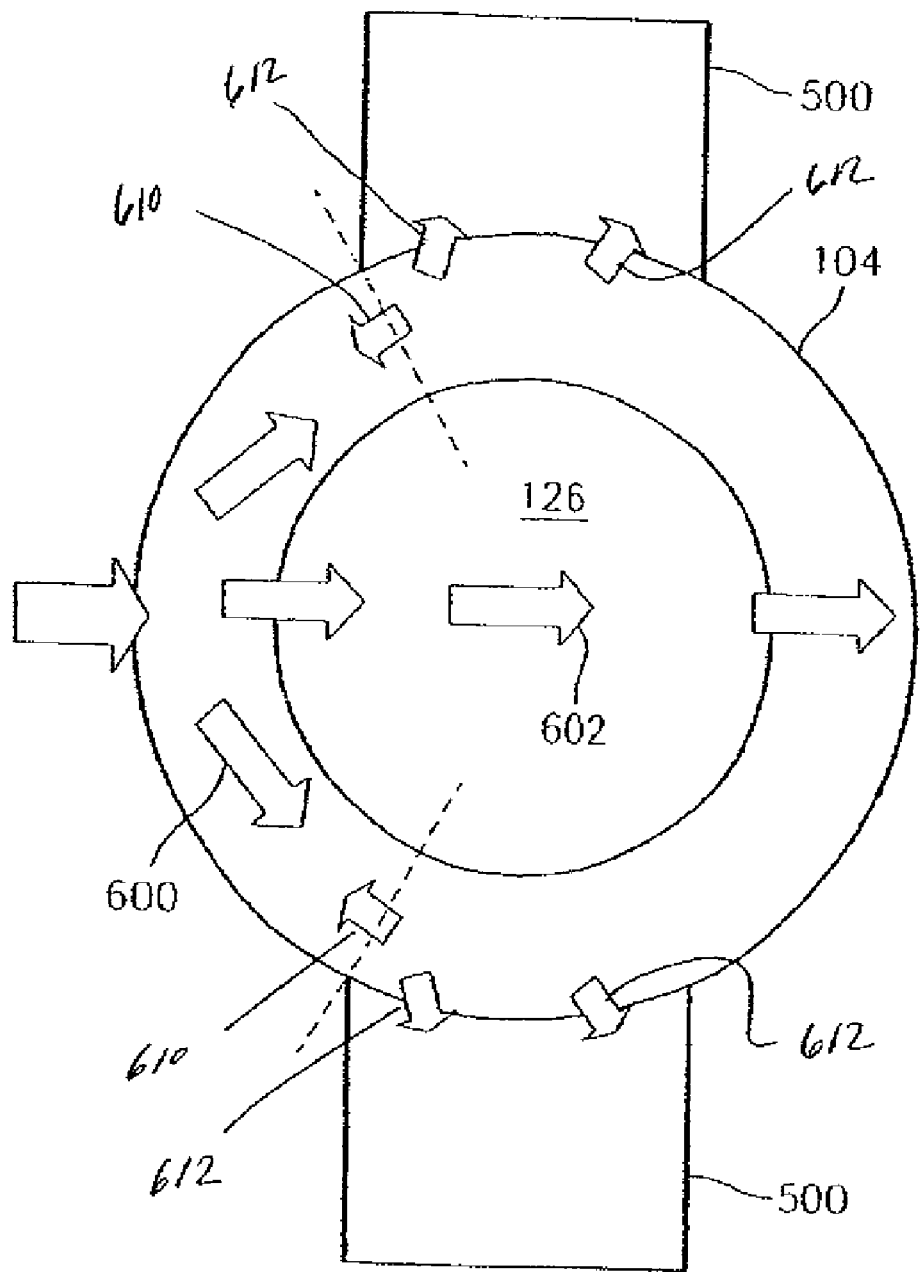
FIG. 24 is a diagram illustrating the flow of ultrasonic energy injected into a pipe with ring-around reducing blocks.

As discussed above and as seen in FIG. 23 and FIG. 24, for various measurements made on pipes 104 the transit time of an ultrasonic wave is determined and a related pipe parameter is derived (e.g. flow velocity). Often the ultrasonic energy is coupled through a pipe 104 wall and then into the confined fluid 126. The signal of interest is the signal 602 that passes thru the fluid 126 (or other material contained in the pipe 104). Sometimes this signal is difficult to see because some of the ultrasonic energy is unavoidably coupled into the pipe 104 wall and travels around the circumference of the pipe 104 wall and ends up on top of the desired signal. This unwanted signal is typically referred to as ring-round signal 600.

By attaching blocks 500 with similar impedance to the pipe 104 to the pipe wall the ring-round signal can be reduced. The blocks 500 reduce the ring-round by basically two methods. First, for a wave 600 traveling in the pipe wall, the block 500 because of its thickness, creates a different impedance and the energy is reflected as signal 610. Second, the energy that is not reflected travels out into the block 500 as signal 612 and does not continue around the pipe 104. Note that the blocks 500 should be attached to the pipe with a solid material because a gel or liquid may not couple out the shear wave.

Figure 25A:
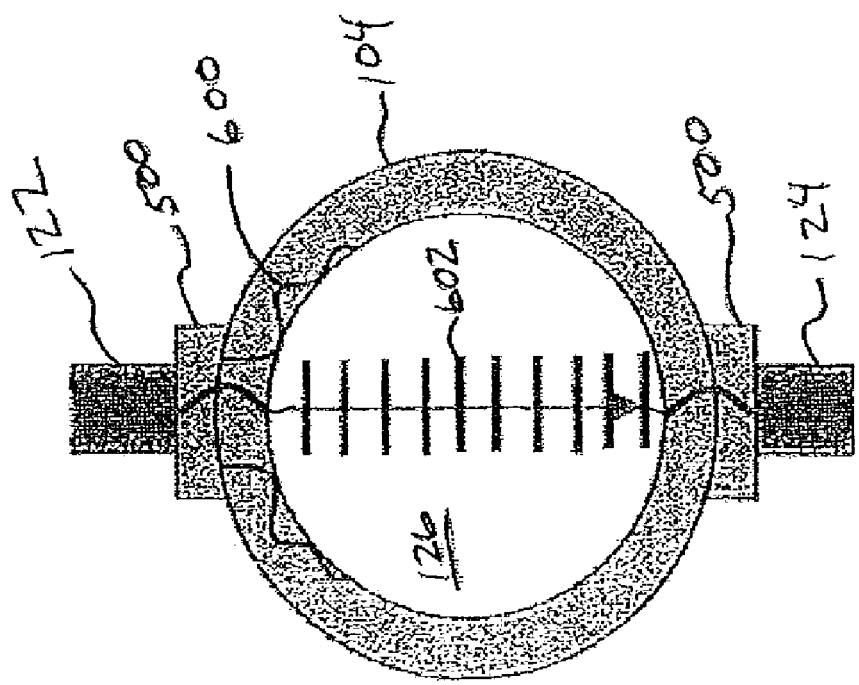
FIG. 25A is a cross-sectional view of a pipe having an ultrasound transmitter and ultrasound receiver affixed thereto and illustrating structurally borne and fluid borne components of an ultrasound signal propagating through the pipe wall and within a process flow in the pipe.
Figure 25B:
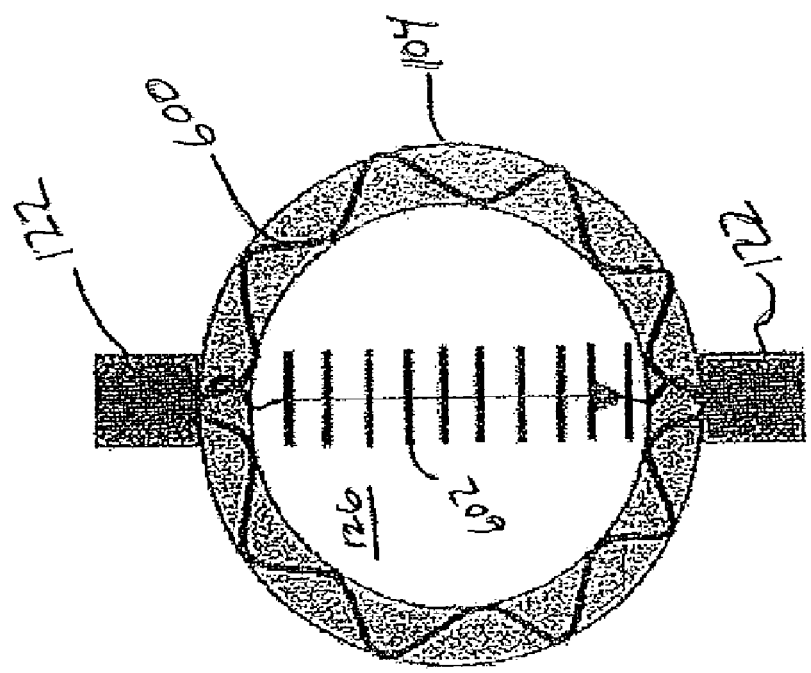
FIG. 25B is a cross-sectional view of a pipe having a pair of blocks affixed to the pipe, an ultrasound transmitter and ultrasound receiver attached to the blocks and illustrating structurally borne and fluid borne components of an ultrasound signal propagating through a pipe wall and within a process flow in the pipe.

In one embodiment, illustrated in FIGS. 25A and 25B, the transmitter 122 emits an ultrasonic signal though the pipe 104 resulting in a structural borne signal component 600 that traverses the pipe wall and a fluid borne signal component 602 that traverses the fluid 126 (or mixture) in the pipe and are both received by the receiver 124 (FIG. 25A). As shown in FIG. 25B, a first one of the blocks 500 is affixed to the pipe 104 between the pipe wall and the ultrasound transmitter 122, and a second one of the blocks 500 is affixed to the pipe 104 between the pipe wall and the receiver 124. As shown in FIG. 25B, the location of the blocks 500 effectively increases the pipe wall thickness in proximity to the transmitter 122 and the receiver 124 to dissipate and substantially eliminate the unwanted ring around signal 600 propagating through the pipe wall. For example, and as is illustrated in FIG. 25B, as the structural borne signal component 600 exits the block 500 the component 600 is substantially minimized and dissipates prior to traversing the circumference of the pipe 104. As such, the embodiment illustrated in FIG. 25B substantially prevents the ring-around signal from reaching the receiver 124.

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An apparatus for damping at least one component of an ultrasonic signal, the apparatus comprising:
    at least one sensor operable to be affixed to an outer surface of a wall of a pipe, the at least one sensor having a transmitter and a receiver orthogonally disposed on opposite sides of the pipe, the transmitter for transmitting the ultrasonic signal in a direction substantially normal to the outer surface of the pipe wall, the transmitted ultrasonic signal including a structural component propagating circumferentially through the pipe wall and a fluid component propagating normally through the pipe wall, the receiver for receiving the ultrasonic signal fluid component; and
    a damping structure operable to be affixed to the pipe and to dampen the structural component of the ultrasonic signal and thereby impede circumferential propagation of the structural component within the pipe wall.

2. The apparatus of claim 1, wherein the damping structure includes a housing secured to the pipe to modify ultrasonic vibrational characteristics of the pipe by increasing a flexural stiffness of the pipe.

3. An apparatus for damping at least one component of an ultrasonic signal, the apparatus comprising:
- at least one sensor affixed to an outer surface of a pipe, the at least one sensor having a transmitter and a receiver, the transmitter for transmitting the ultrasonic signal, the transmitted ultrasonic signal including a structural component propagating through a wall of the pipe and a fluid component propagating through a process flow in the pipe, the receiver for receiving at least one of the transmitted components of the ultrasonic signal; and
- a damping structure affixed to the pipe and damping the structural component of the ultrasonic signal to impede propagation of the structural component to the receiver;
- wherein the damping structure includes a housing secured to the pipe to modify ultrasonic vibrational characteristics of the pipe by increasing a flexural stiffness of the pipe; and
- wherein the housing contacts and reinforces selective areas of the pipe to provide a diaphragm including reinforced are as and unreinforced areas, wherein the unreinforced areas are disposed about and in proximity to the transmitter and the receiver.

4. The apparatus of claim 3, wherein a resonant frequency of the diaphragm coincides with a resonant frequency of a maximum transmission of the ultrasonic signal.

5. The apparatus of claim 3, wherein a diameter of the diaphragm is twice a thickness of the wall of the pipe.

6. The apparatus of claim 3, wherein the housing further includes viscoelastic material to provide multiple impedance changes and alternate energy dissipation paths to augment damping of the structural component.

7. The apparatus of claim 6, wherein the housing includes slots for retaining the viscoelastic material.

8. An apparatus for damping at least one component of an ultrasonic signal, the apparatus comprising:
- at least one sensor affixed to an outer surface of a pipe, the at least one sensor having a transmitter and a receiver, the transmitter for transmitting the ultrasonic signal, the transmitted ultrasonic signal including a structural component propagating through a wall of the pipe and a fluid component propagating through a process flow in the pipe, the receiver for receiving at least one of the transmitted components of the ultrasonic signal; and
- a damping structure affixed to the pipe and damping the structural component of the ultrasonic signal to impede propagation of the structural component to the receiver;
- wherein the damping structure includes a plurality of film assemblies applied to an outer surface of the pipe, each of the film assemblies includes a substrate and a selectively tunable circuit, wherein the circuit is tuned to attenuate structural vibration of the pipe and the structural component propagating in the wall of the pipe.

9. The apparatus of claim 8, wherein the substrate is comprised of a piezoelectric film and the tunable circuit is comprised of a RLC circuit.

10. The apparatus of claim 1, wherein the damping structure includes a plurality of blocks affixed to the pipe.

11. The apparatus of claim 10, wherein the blocks and the pipe wall are at a different impedance such that the structural component of the ultrasonic signal is at least one of reflected back toward the transmitter and propagated through a dissipation path in the blocks and away from the receiver.

12. The apparatus of claim 10, wherein the blocks are disposed axially along the pipe between the transmitter and the receiver.

13. The apparatus of claim 10, wherein one of the blocks is disposed between the pipe wall and the transmitter and another of the blocks is disposed between the pipe wall and the receiver.

14. The apparatus of claim 1, further including:
- a processor coupled to the receiver and sampling the received components of the ultrasonic signal, the processor processing the sampled signal to determine a parameter of the process flow in the pipe.

15. An apparatus for damping at least one component of an ultrasonic signal, the apparatus comprising:
- a plurality of damping blocks disposed axially along an outer surface of a wall of a pipe;
- a plurality of sensors, each sensor having a transmitter coupled to one of the damping blocks and a receiver coupled to one of the damping blocks, wherein the transmitter and the receiver of each sensor are orthogonally disposed on opposite sides of the pipe, the transmitter for transmitting the ultrasonic signal, the transmitted ultrasonic signal including a structural component propagating circumferentially through the pipe wall and a fluid component propagating in a direction normal to the pipe wall, through the pipe wall, the receiver for receiving the ultrasonic signal fluid component; and
- a processor coupled to the receivers of the plurality of sensors and sampling the received components of the ultrasonic signal, the processor processing the sampled signal to determine a parameter of the process flow in the pipe.

16. The apparatus of claim 15, wherein each of the damping blocks is operable to be affixed to the pipe and to dampen the structural component of the ultrasonic signal and thereby impede circumferential propagation of the structural component within the pipe wall.

17. The apparatus of claim 16, wherein the housing contacts and reinforces selective areas of the pipe to provide a diaphragm including reinforced areas and unreinforced areas, wherein the unreinforced areas are disposed about and in proximity to the transmitter and the receiver.

* * * * *